(12) United States Patent
Romo et al.

(10) Patent No.: US 10,561,514 B2
(45) Date of Patent: Feb. 18, 2020

(54) ORTHOTIC SYSTEM

(71) Applicant: Ossur Iceland ehf, Reykjavik (IS)

(72) Inventors: Harry Duane Romo, Foothill Ranch, CA (US); Jonathan Walborn, Foothill Ranch, CA (US); Jamal Abdul-Hafiz, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 438 days.

(21) Appl. No.: 15/375,395

(22) Filed: Dec. 12, 2016

(65) Prior Publication Data
US 2017/0165095 A1 Jun. 15, 2017

Related U.S. Application Data

(60) Provisional application No. 62/265,506, filed on Dec. 10, 2015.

(51) Int. Cl.
A61F 5/01 (2006.01)
(52) U.S. Cl.
CPC ................ A61F 5/0113 (2013.01)
(58) Field of Classification Search
CPC .... A61F 5/0111; A61F 5/0113; A61F 5/0127; A61F 5/0195; A61F 5/14; A61F 13/023; A61F 13/12; A61F 13/14; A43B 7/1405; A43B 7/18; A43B 7/20; A43B 7/28; A43B 7/32
See application file for complete search history.

(56) References Cited

U.S. PATENT DOCUMENTS

| 114,669 | A | 5/1871 | Grant |
| 433,227 | A | 7/1890 | Beacock |
| 735,860 | A | 8/1903 | Darby |
| 839,223 | A | 12/1906 | Stevens |
| RE13,026 | E | 10/1909 | Arrowsmith |
| 988,942 | A | 4/1911 | Krech et al. |
| 1,078,708 | A | 11/1913 | Thomas |
| 1,334,596 | A | 3/1920 | Crouch |
| 1,477,750 | A | 12/1923 | Endrea |
| 1,656,322 | A | 1/1928 | Fischer |
| 1,769,781 | A | 7/1930 | Harrison |

(Continued)

FOREIGN PATENT DOCUMENTS

| DE | 662799 C | 7/1938 |
| DE | 831872 C | 2/1952 |

(Continued)

OTHER PUBLICATIONS

International Search Report from PCT Application No. PCT/US2016/066094, dated Feb. 28, 2017.

Primary Examiner — Kari K Rodriquez
(74) Attorney, Agent, or Firm — Workman Nydegger

(57) ABSTRACT

An orthosis includes a footplate having a heel portion, a midfoot portion, and a longitudinal axis extending between the heel and midfoot portions. A first deflection zone is defined along a length of the footplate anterior of the heel portion and through which the footplate is arranged to flex during gait to accommodate dorsiflexion of a foot of a user positioned on the footplate. At least one strut is connected to the heel portion of the footplate and extends upwardly therefrom and a connecting portion connects the at least one strut to the heel portion.

18 Claims, 18 Drawing Sheets

(56) References Cited

U.S. PATENT DOCUMENTS

| | | |
|---|---|---|
| 1,957,695 A | 5/1934 | Chiappetta |
| 2,217,882 A | 10/1940 | Andersen |
| 2,492,920 A | 12/1949 | Koster |
| 2,755,569 A | 7/1956 | Guy |
| 2,847,991 A | 8/1958 | Andrews |
| 2,949,111 A | 8/1960 | Ruotoistenmaki |
| 3,086,522 A | 4/1963 | Frohmader |
| 3,171,407 A | 3/1965 | Rogers |
| 3,304,937 A | 2/1967 | Callender, Jr. |
| 3,345,654 A | 10/1967 | Noble |
| 3,523,526 A | 8/1970 | Phelps |
| 3,557,782 A | 1/1971 | Wafer |
| 3,584,622 A | 6/1971 | Domenico |
| 3,589,359 A | 6/1971 | Hill |
| 3,618,946 A | 11/1971 | Lee |
| 3,779,654 A | 12/1973 | Horne |
| RE27,957 E | 4/1974 | Larson |
| 3,976,059 A | 8/1976 | Lonardo |
| 4,520,581 A | 6/1985 | Irwin et al. |
| 4,651,445 A | 3/1987 | Hannibal |
| RE32,698 E | 6/1988 | Brown |
| 4,813,157 A | 3/1989 | Boisvert et al. |
| 4,938,777 A | 7/1990 | Mason et al. |
| 4,979,252 A | 12/1990 | Daley |
| RE33,648 E | 7/1991 | Brown |
| RE33,762 E | 12/1991 | Lonardo |
| 5,216,825 A | 6/1993 | Brum |
| 5,219,324 A | 6/1993 | Hall |
| 5,226,875 A | 7/1993 | Johnson |
| 5,269,748 A | 12/1993 | Lonardo |
| 5,298,013 A | 3/1994 | Lonardo |
| 5,372,576 A | 12/1994 | Hicks |
| 5,431,624 A | 7/1995 | Saxton et al. |
| 5,569,173 A | 10/1996 | Varn |
| 5,569,174 A | 10/1996 | Varn |
| 5,716,336 A | 2/1998 | Hines et al. |
| 5,778,562 A | 7/1998 | Karl-Heinz |
| 5,799,659 A | 9/1998 | Stano |
| 5,817,041 A | 10/1998 | Bader |
| 5,897,515 A | 4/1999 | Willner et al. |
| 5,940,994 A | 8/1999 | Allen |
| 5,944,679 A | 8/1999 | Detoro |
| 5,994,245 A | 11/1999 | Marier et al. |
| 6,146,344 A | 11/2000 | Bader |
| 6,205,685 B1 | 3/2001 | Kellerman |
| 6,543,158 B2 | 4/2003 | Dieckhaus |
| 6,557,273 B2 | 5/2003 | Polifroni |
| 6,560,902 B1 | 5/2003 | Eschweiler |
| 6,676,618 B2 | 1/2004 | Andersen |
| 6,889,452 B2 | 5/2005 | Ailey et al. |
| 6,945,947 B2 | 9/2005 | Ingimundarson et al. |
| 7,112,180 B2 | 9/2006 | Guenther |
| 7,112,181 B1 | 9/2006 | Detoro et al. |
| 7,266,910 B2 | 9/2007 | Ingimundarson |
| 7,270,644 B2 | 9/2007 | Ingimundarson |
| 7,722,556 B2 | 5/2010 | Warner |
| 7,815,587 B2 | 10/2010 | Korner et al. |
| 8,202,239 B2 | 6/2012 | Wilkerson |
| 8,465,445 B2 | 6/2013 | George |
| 2004/0186401 A1 | 9/2004 | Guenther |
| 2005/0054959 A1* | 3/2005 | Ingimundarson .... A43B 13/026 602/5 |
| 2005/0054963 A1 | 3/2005 | Ingimundarson |
| 2007/0135746 A1* | 6/2007 | Korner ................. A61F 5/0111 602/27 |
| 2007/0197948 A1 | 8/2007 | Ingimundaron et al. |
| 2008/0319361 A1 | 12/2008 | Messer |
| 2012/0184887 A1 | 7/2012 | Wynne et al. |
| 2014/0257162 A1 | 9/2014 | Falkenman et al. |
| 2015/0018734 A1 | 1/2015 | Benford |
| 2015/0065934 A1 | 3/2015 | Bader |
| 2015/0150709 A1 | 6/2015 | Ljubimir et al. |
| 2015/0164179 A1 | 6/2015 | Walborn et al. |
| 2015/0305911 A1 | 10/2015 | Schroeder |

FOREIGN PATENT DOCUMENTS

| | | |
|---|---|---|
| DE | 1693315 U | 2/1955 |
| DE | 1133278 B | 7/1962 |
| DE | 4214831 A1 | 11/1993 |
| DE | 9319050 U1 | 2/1994 |
| DE | 19722118 A1 | 2/1999 |
| DE | 29909981 U1 | 9/1999 |
| DE | 19905544 A1 | 8/2000 |
| EP | 0931525 A1 | 7/1999 |
| EP | 2363100 A1 | 9/2011 |
| GB | 2188550 A | 10/1987 |
| JP | H0723803 A | 1/1995 |
| WO | 9205751 A1 | 4/1992 |
| WO | 9728762 A1 | 8/1997 |
| WO | 02096328 A1 | 12/2002 |
| WO | 03002042 A1 | 1/2003 |
| WO | 2011128588 A1 | 10/2011 |

* cited by examiner

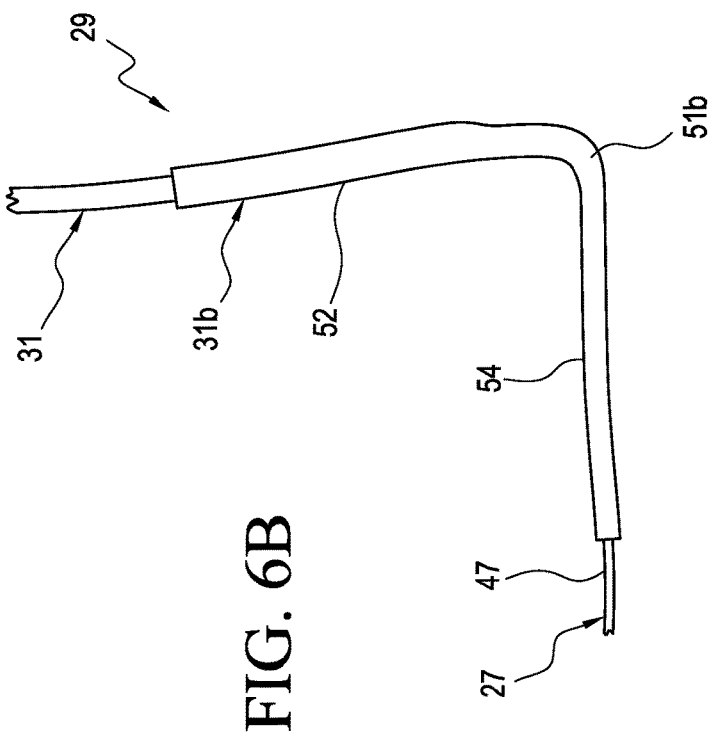
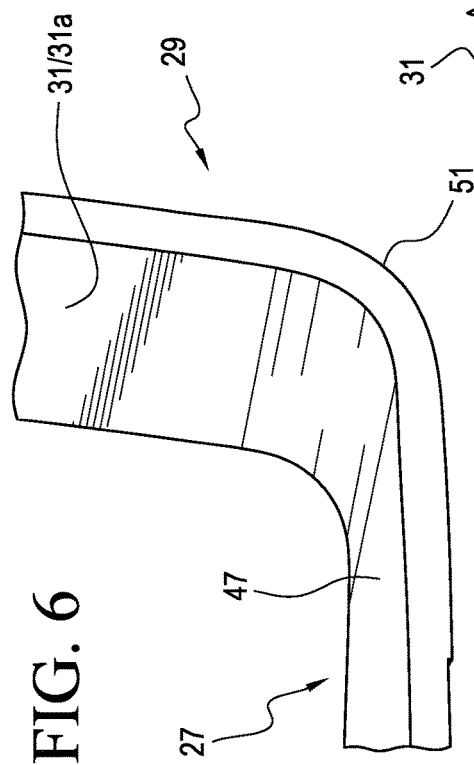
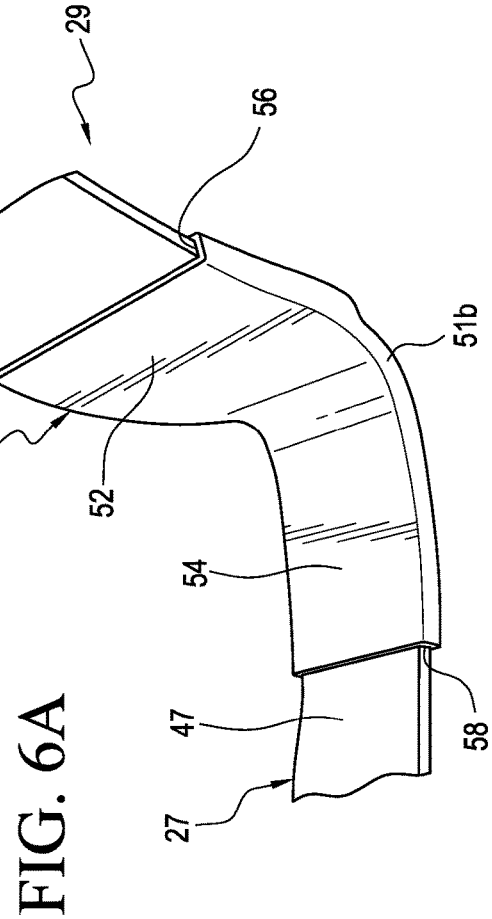
FIG. 6
FIG. 6A
FIG. 6B

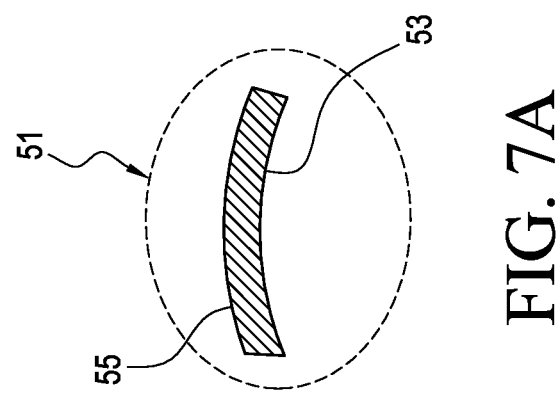
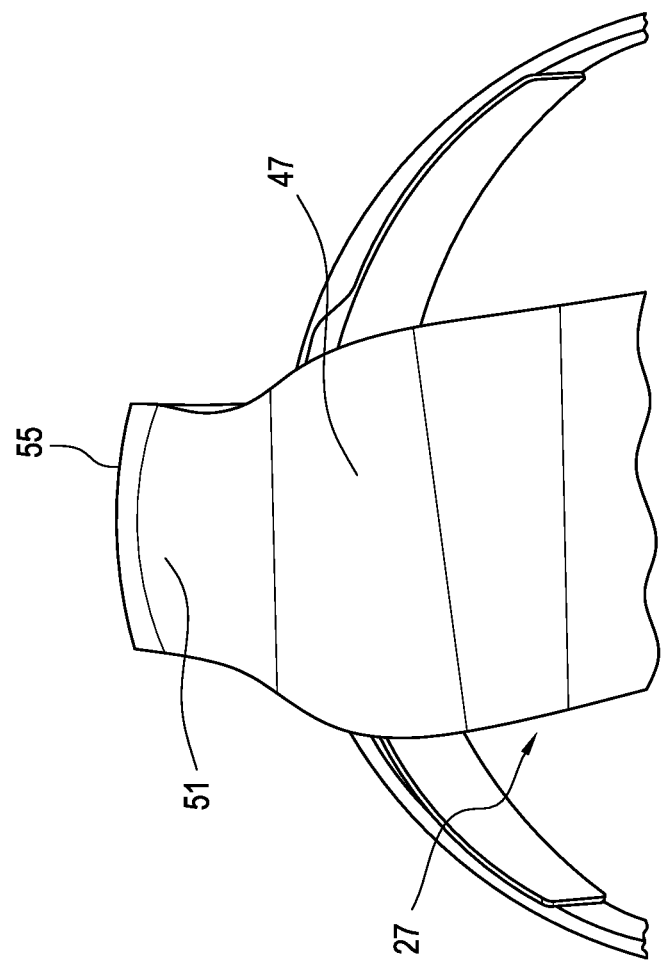

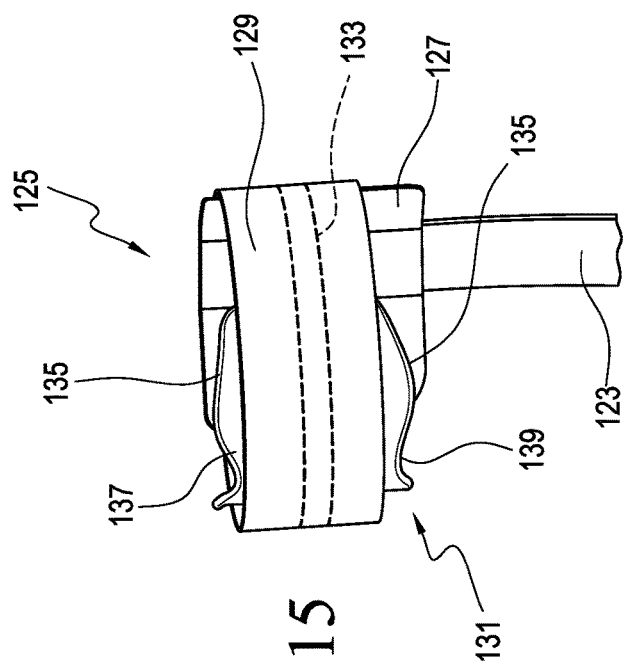
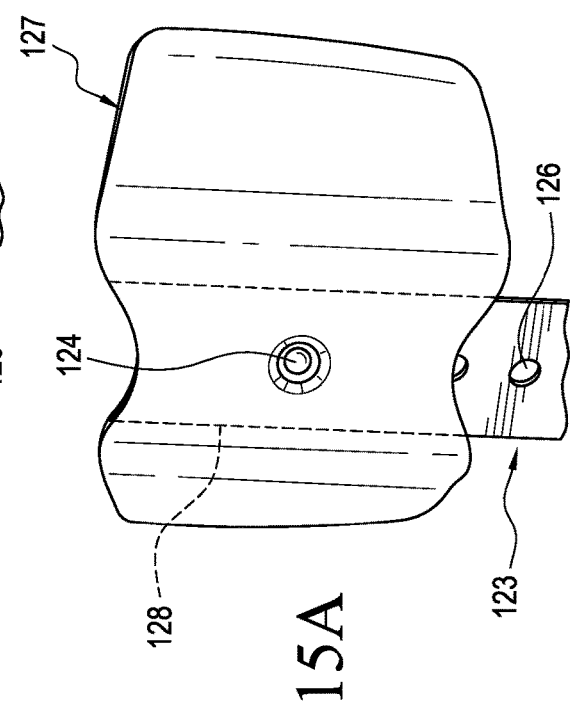
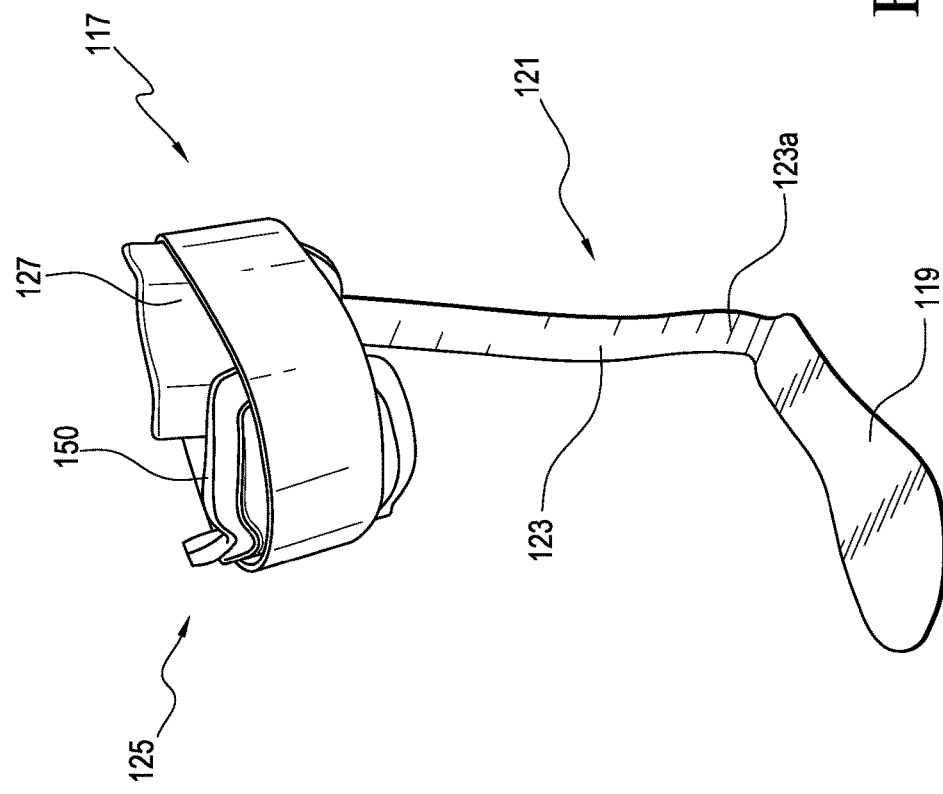
FIG. 15
FIG. 15A
FIG. 14

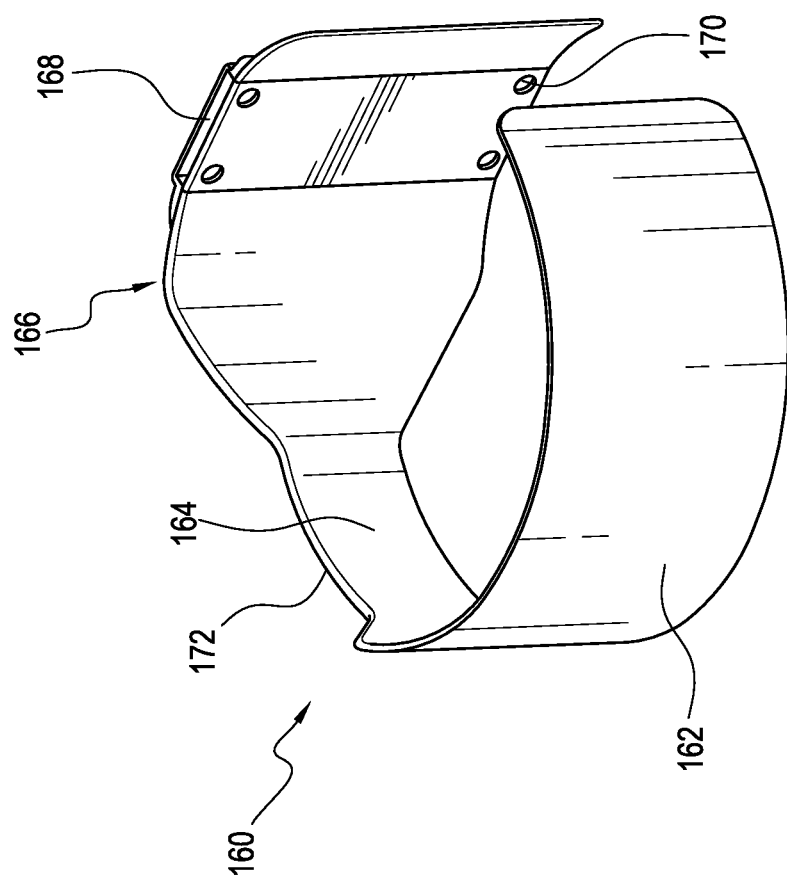

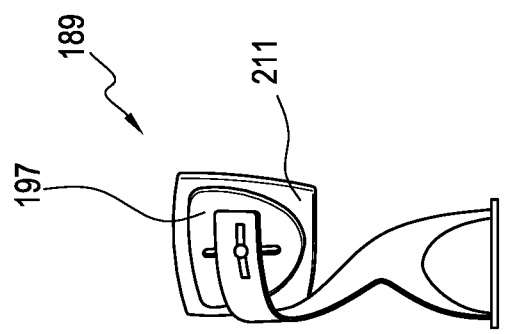
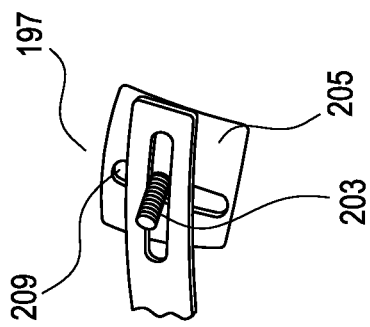
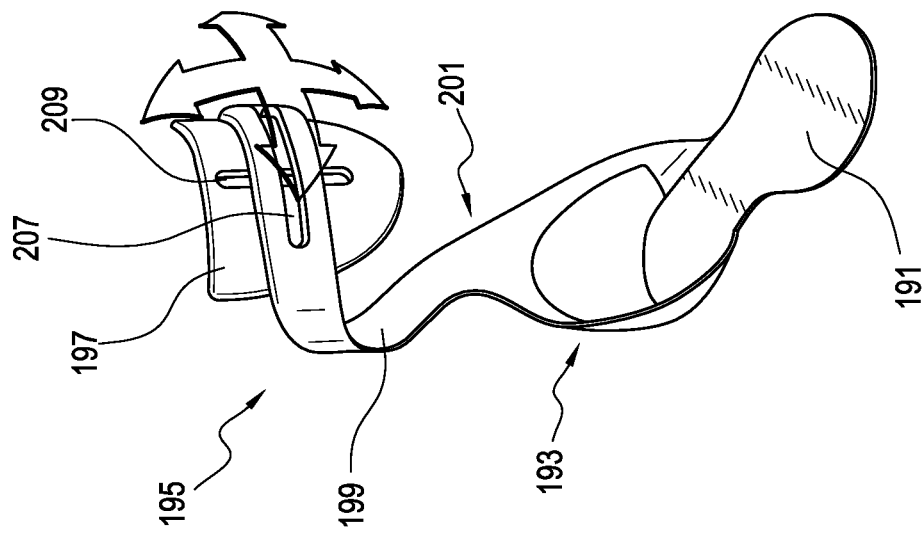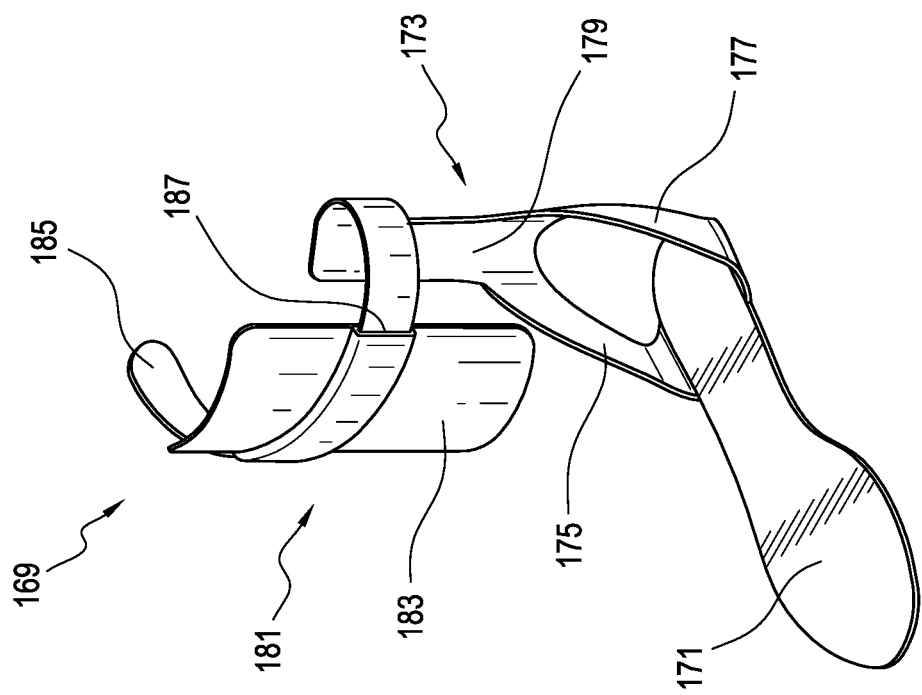

ORTHOTIC SYSTEM

TECHNICAL FIELD

The disclosure relates to an orthotic system for assisting the biomechanics of the foot, ankle, and/or lower leg, and more specifically to an orthotic system including an ankle-foot orthosis ("AFO").

BACKGROUND

AFO devices are designed to correct gait impairments for patients by stabilizing and securing the ankle-foot complex during gait. AFOs can be required for patients affected by a wide range of conditions including direct injury to the dorsiflexors, the common peroneal, the sciatic nerves, or the neural pathways that supply them. AFOs are also used to treat gait impairments resulting from conditions such as cerebral palsy, multiple sclerosis, or scoliosis, and are also common among subjects post-stroke who cannot properly dorsiflex their ankle or extend their toes.

The process of fitting an AFO to a patient is typically done by a skilled clinician who selects an AFO based on the patient's condition, the patient's foot/shoe size, the patient's activity level and/or the patient's weight. If appropriate, the patient is fitted with a standard, off-the-shelf ("OTS") AFO. However, for patients with deformities or gait irregularities, a custom AFO is often necessary.

Once fitted, the AFO is often placed into the patient's shoe, underneath an insole. The insole can be a standard, unmodified insole or it can provide some corrective support, as needed.

Many known AFOs, both OTS and custom, concentrate on the ankle and knee biomechanics while aligning the patient's foot parallel to the patient's longitudinal axis or straight ahead from back to front. For instance, known AFOs align the user's foot straight ahead during gait. Most people however do not walk with their feet pointed straight ahead. Rather, most people walk with their feet externally rotated. Thus, conventional AFOs are known to resist typical foot rotation during gait. This can be problematic and even detrimental to a patient, adding stress and causing coronal plane or torsional loading on the knee as well as instability and discomfort.

Such unnatural foot motion can also cause foot and leg fatigue because it conflicts with normal gait of a patient, requiring the wearer to adjust or correct the position of the wearer's foot while ambulating. It also can create awkward pressure points on the patient's lower leg and/or foot as a result of the AFO being urged unnaturally against the wearer's lower leg and/or foot while ambulating.

Many known AFOs also flex in such a way that they impinge upon the wearer's heel, which in turn, can cause discomfort at the distal attachment of the Achilles tendon or other problems during use.

In addition to resisting typical foot rotation during gait, existing AFO designs that incorporate posterior struts do not easily allow for adaptations for anterior components, using only fabric straps wrapped around the anterior aspect of the calf. However, as gait motion is forwardly (anterior), a rigid posterior strut with a flexible anterior element can be counter-productive and can lead to complications during gait where a patient tends to lean back in the AFO, negatively impacting balance and stability. Furthermore, fabric straps secured too tightly can lead to lines of pressure from the straps resulting in discomfort and, in extreme cases, reduction in blood flow to the limb.

Existing AFO designs that incorporate either medial or lateral struts that transition to an anterior component often have the limitation of transferring force from the calf, which is normal to the anterior shell, into the medial or lateral strut, which is 90 degrees from the anterior shell, to a footplate, providing counterforce from the ground, which is again 90 degrees from the strut. This often results in force transfer between the different elements being not only not normal to the gait motion, but also at disadvantageous angles, resulting in gait inefficiency as well as a tendency to fail prematurely. It may also feel counter-intuitive or unnatural for new users, who are unfamiliar with the typical feeling of these products.

Furthermore, OTS AFO designs are not adjustable and cannot accommodate a large range of users, while custom AFO designs are time-consuming and expensive to produce.

There is Thus a Need for an Orthotic System that is More Comfortable, Versatile, and Encourages More Natural Biomechanics of the Foot, Ankle, and Lower Leg.

SUMMARY

Embodiments of the orthotic system advantageously allow users to experience a more comfortable and natural gait by accommodating voluntary flexion of the foot and typical foot rotation during gait. According to an embodiment, the orthotic system comprises an orthosis including a footplate having a heel portion, a midfoot portion, and a longitudinal axis extending between the heel and midfoot portions. A first deflection zone is defined along a length of the footplate anterior of the heel portion and through which the footplate is arranged to flex during gait to accommodate dorsiflexion of a foot of a user positioned on the footplate. At least one strut is connected to the heel portion of the footplate and extends upwardly therefrom and a connecting portion connects the at least one strut to the heel portion.

According to an embodiment, the first deflection zone is arranged to direct flexing or deflection of the footplate to under the ball or heads of the metatarsal bones of the foot. During toe-off, loading on the footplate causes the footplate to bend or flex through the first deflection zone. This allows a forefoot portion of the footplate to deflect toward the at least one strut under the toes of the user, providing dorsiflexion to the forefoot portion. The flexibility of the footplate through the first deflection zone helps prevent or limit the footplate from forcing the user's toes into the top of a shoe or boot during gait. It also advantageously limits or prevents lateral pivoting of the user's foot during gait.

The first deflection zone can be defined at least in part by a portion of the forefoot portion that is thinner than the midfoot and/or heel portions. The first deflection zone can also be defined at least in part by a layered or laminate structure of the footplate through the first deflection zone. For instance, the structure of the footplate through the first deflection zone can include top and bottom layers comprising a fiberglass composite weave, and one or more layers comprising unidirectional carbon fiber composite located between the top and bottom layers. The layers of fiberglass are more flexible than the unidirectional carbon fiber composite, providing greater flexibility through the first deflection zone.

According to an embodiment, a second deflection zone is defined along a length of the at least one strut proximal of the connecting portion. The location and/or amount the at least one strut flexes through the second deflection zone can be controlled by varying the thickness of the posterior strut and/or by changing the cross-sectional area or shape of the strut in the second deflection zone. When a user moves the foot toward plantarflexion, the downward force on the footplate can cause strut to bend or flex through the second deflection zone. This in turn allows at least the forefoot portion and/or the midfoot portion of the footplate to move away from the at least one strut. This movement advantageously allows a user to experience common activities, like driving a car or riding a bicycle, where plantarflexion is necessary.

According to an embodiment, the connecting portion includes a curve or curved cross section across a width of the connecting portion. This enhances the comfort and fit of the orthosis. It also creates a more rigid section of the at least one strut at or near the heel, which resists flexing during use. This beneficially limits undesired flexing at the heel during use, which, in turn, helps prevent the at least one strut from impinging on or injuring the heel during use of the orthosis.

According to an embodiment, the footplate further defines a supportive zone that is rigid or semi-rigid posterior of the first deflection zone. The supportive zone can extend below a center of mass of the user's foot and can be arranged to maintain the foot in a neutral or near-neutral position during the swing phase. This beneficially helps to reduce the likelihood of the foot dragging or catching during the swing phase. It also reduces or eliminates the need for the user to lift or swing the hip during gait.

According to an embodiment, the at least one strut comprises a posterior strut and the connecting portion is positioned lateral of the longitudinal axis of the footplate. This has the advantage of better maintaining the natural offset or misalignment between the rotation axis of the user's ankles, and the rotation axes of the user's knees and hip. It also encourages the user to walk more normally and comfortably rather than creating a forced and unnatural anatomical alignment as in the prior art. For instance, known posterior strut AFOs include a posterior strut that is generally positioned perpendicular to the longitudinal axis of the foot on the footplate or parallel to the rotation axes of the patient's knee and/or hip. Such positioning tends to cause unnatural or potentially harmful anatomical alignment between the user's ankle and knee and hip.

BRIEF DESCRIPTION OF THE DRAWINGS

These and other features, aspects, and advantages of the present disclosure will become better understood regarding the following description, appended claims, and accompanying drawings.

FIG. 6 is a partial side view of the system in FIG. 4.

FIG. 6A is a partial perspective view of an orthotic system according to another embodiment.

FIG. 6B is a side view of the system in FIG. 6A.

FIG. 7 is a partial bottom view of the system in FIG. 4.

FIG. 7A is a cross section view of the posterior strut shown in FIG. 4.

FIG. 14 is a perspective view of an orthotic system according to another embodiment.

FIG. 15 is a detailed view of the securing device shown in FIG. 14.

FIG. 15A is a detailed view of the securing device according to another embodiment.

FIG. 20 is a perspective view of a securing system according to another embodiment.

FIG. 21 is a perspective view of an orthotic system according to another embodiment.

FIG. 22 is a perspective view of an orthotic system according to another embodiment.

FIG. 22A is a front view of the system shown in FIG. 22.

FIG. 22B is a detailed view of the anterior shell shown in FIG. 22.

DETAILED DESCRIPTION OF VARIOUS EMBODIMENTS

Figure 2:
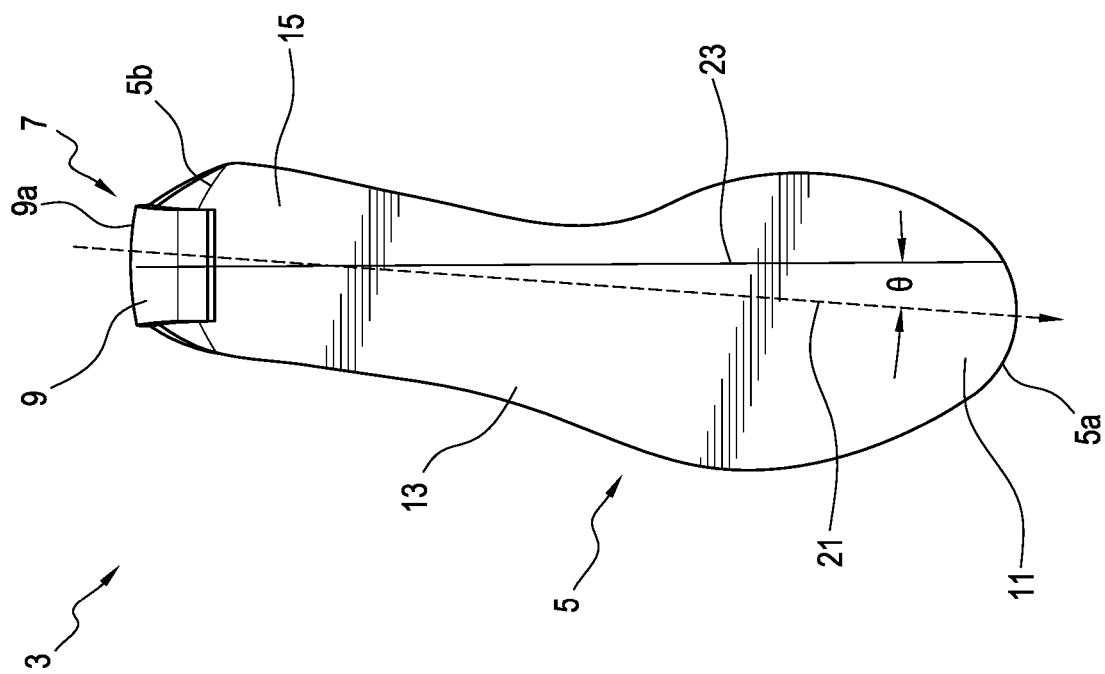
FIG. 2 is a top view of the system in FIG. 1.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112(f).

In many of the embodiments described herein, the orthosis includes a leg support and a footplate defining a line of progression extending from a heel portion through at least a midfoot portion of the footplate. In some embodiments, the line of progression extends from the heel portion to the midfoot portion to a forefoot portion of the footplate. The line of progression basically defines a position curve of center of mass along the foot during a stance phase.

Exemplary embodiments of the orthosis are provided for assisting or controlling the biomechanics of the foot, ankle, and/or lower leg. Features that are provided on one side of the orthosis can easily be provided on the other side of the orthosis. In this manner, it is intended that the exemplary embodiments of the orthosis described herein may be used on either right or left lower legs, with any appropriate reconfiguration of components that is deemed necessary for the proper fit and function of the orthosis for the purpose of assisting or controlling the biomechanics of the left or right foot, ankle, and/or lower leg.

While various embodiments described herein may have different properties and structural configurations, each footplate generally and/or preferably possesses the above-mentioned portions. Further, the footplate may be divided into more portions, however, for simplicity and sake of explanation, the following disclosure will remain limited to the above-mentioned portions.

Embodiments of the orthosis may be modified to include a variety of different layers, thicknesses, lengths, and shapes. It is to be understood that it is envisioned that as with users having different foot sizes and shapes, the orthotic footplate may likewise be modified to define such corresponding sizes and shapes.

Reference will be made herein to the gait cycle of a human being. The gait cycle is broken down into two components: the swing phase and the stance phase.

The swing phase lasts from the point when the toe leaves the ground until the moment when the heel comes into contact with the ground. At toe-off, the foot is in a supinated position, and to assist in clearing the toe from the ground, it originally pronates. The remainder of the swing phase, the foot supinates prior to bringing the heel to the ground for the stance phase of the gait cycle.

The stance phase may be broken down into three portions: contact, midstance, and propulsion. During the contact portion, the foot acts to absorb the shock of each step. The foot pronates to become more flexible in order to prevent transmission of the full force of each step to more proximal structures. During the midstance portion, the foot begins to supinate, transforming from a flexible shock absorber to a rigid level for propulsion.

This period ends when the heel lifts off of the ground, and the propulsive period begins. In the propulsion phase, the foot continues to supinate, propelling the body forward and ends with toe-off.

Figure 1:
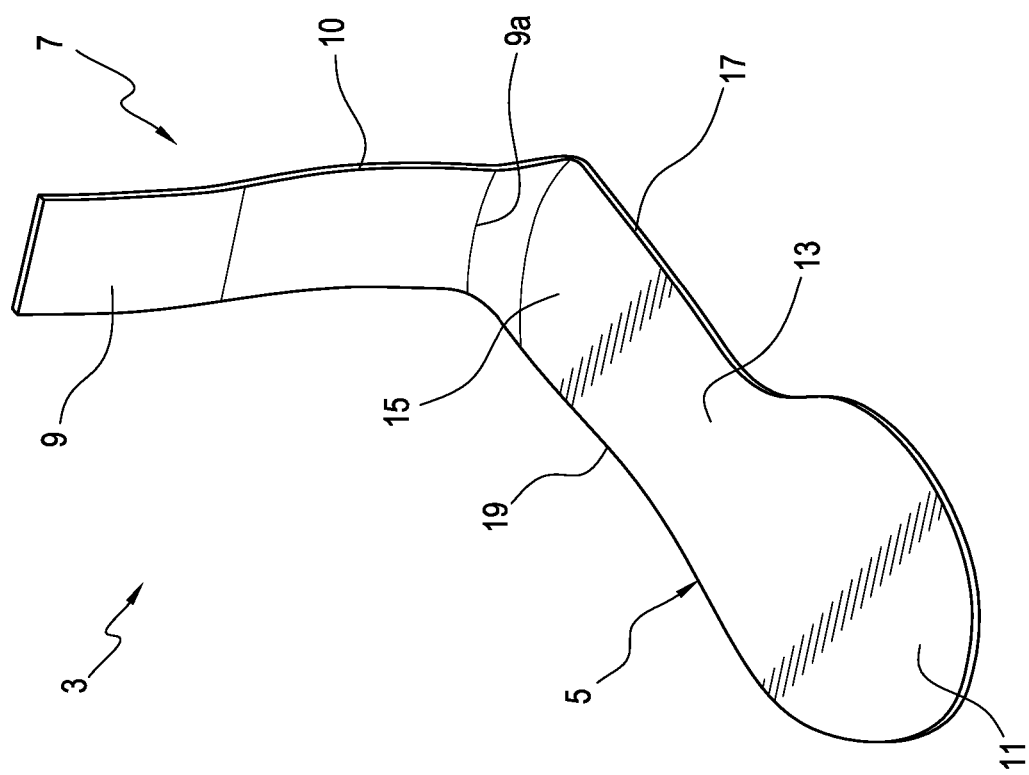
FIG. 1 is a perspective view of an orthotic system according to an embodiment.
Figure 3:
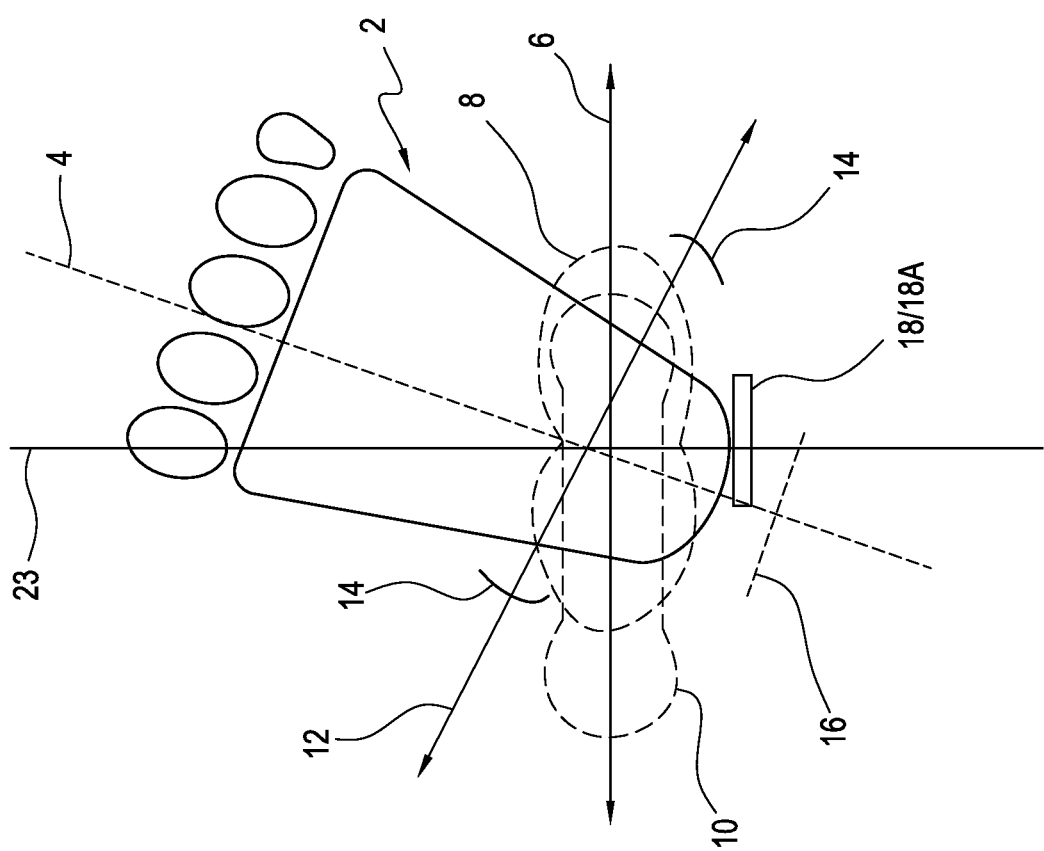
FIG. 3 is a schematic top view of the system in FIG. 1 in use.

FIGS. 1-3 show an orthotic system comprising an orthosis 3 according to an embodiment. The orthosis 3 is an AFO adapted to assist the biomechanics of the foot, ankle, and lower leg. The orthosis 3 includes a footplate 5 and a leg support 7 extending upwardly from the footplate 5. The footplate 5 and the leg support 7 can be substantially formed as a single unit.

The leg support 7 includes a posterior strut 9 arranged to extend along the back of the user's lower leg. The leg support 7 can have any suitable shape and its length may be varied depending on the application and the user.

According to a variation, the posterior strut 9 can form a curve or curved profile 10 along a length thereof corresponding to a heel area of the user. The curved profile 10 advantageously can better accommodate the shape of the heel. The curved profile 10 can also improve fit of the posterior strut 9 within a shoe, as it conforms better to the heel shape in a typical shoe. As such, the orthosis 3 provides a more comfortable fit to a user than prior art AFOs. The posterior strut 9 can extend along a generally straight line. In other embodiments, the posterior strut 9 can extend along a generally straight line above the heel or can be curved to generally mimic user anatomy.

The footplate 5 defines a forefoot portion 11, a midfoot portion 13, and a heel portion 15. The footplate 5 can have a peripheral shape (including medial and lateral edges 17, 19) that generally corresponds to the shape of a user's foot (not shown) and sized to fit inside a shoe.

The footplate 5 can provide different areas of stiffness and/or flexibility so as to redistribute forces applied to the foot. For instance, the footplate 5 can increase the stability of the foot, release energy and propel a user's foot and leg at toe-off. Moreover, the footplate 5 can raise a user's toes for clearance during the swing phase as discussed below. The configuration of the footplate can result in energy storage and energy release as it undergoes flexion and deflexion during a user's gait.

As seen in FIG. 2, the footplate 5 defines a longitudinal axis 21 extending between the heel portion 15 and at least the midfoot portion 13. For example, the longitudinal axis 21 can extend between an anterior or toe end 5a, which can correspond to the forefoot portion 11, and a posterior end or heel end 5b, which can correspond to the heel portion 15. Anterior generally means being located toward the front of a structure and posterior generally means being located toward the rear or back of a structure.

In addition, the footplate 5 defines a line of progression 23 that extends from the heel portion 15 through the midfoot portion 13, and through the forefoot portion 11. It should be appreciated that the footplate 5 can be constructed in any suitable manner. For instance, the footplate 5 can be sized and configured to terminate under the ball of a user's foot.

The posterior strut 9 is connected to the heel portion 15 of the footplate 5 via a connecting portion 9a of the posterior strut 9. According to a variation, the connecting portion 9a is positioned on the heel portion 15 such that when the orthosis 3 is worn by a user, the longitudinal axis 21 of the footplate 5 is rotated or turned relative to the longitudinal axis of the user, which, in turn, forms an angle θ between the longitudinal axis 21 and the line of progression 23 of the footplate 5. "Internally rotated" or "externally rotated" is the angle θ between the line of progression 23 and the longitudinal axis 21 of the footplate 5. Angle θ is zero if the longitudinal axis 21 is parallel to the line of progression 23 or longitudinal axis of the user. Angle θ is positive or externally rotated when the longitudinal axis 21 is on the lateral side of the line of progression 23 or pointed away from the longitudinal axis of the user. Angle θ is negative or internally rotated when the longitudinal axis 21 is on the medial side of the line of progression 23 or pointed toward the longitudinal axis of the user.

Known AFOs are designed to align the user's foot parallel to the longitudinal axis of the user (e.g., with an angle θ of zero). However, most patients do not walk with their feet pointed straight ahead. Rather, most patients walk with their feet externally rotated. More specifically, most patients walk with their feet externally rotated between about 5 degrees and about 7 degrees or exorotated. By aligning the patient's foot parallel with the longitudinal axis of the user, known AFOs add stress and discomfort to the user as the user ambulates. Such stresses may cause undesirable biomechanical compensations or may adversely affect recuperation. Further, this can cause foot and leg fatigue because the action of the AFO conflicts with the normal motion of the user's foot, requiring the user to adjust or correct the position of the user's foot and/or causing muscle imbalances in the foot and/or leg.

Referring briefly to FIG. 3 and for further ease of understanding, most patients walk with the foot 2 externally rotated or with the longitudinal axis 4 of the foot 2 externally rotated between about 5 degrees and about 7 degrees relative to the line of progression 23. During natural gait, the rotation axes 6 of the patient's knee 8 and/or hip 10 is generally perpendicular to the line of progression 23 while the rotation axis 12 of the patient's ankle 14 is generally perpendicular to the longitudinal axis 4 of the foot, resulting in a natural offset or misalignment between the rotation axes 6 of the knee 8 and/or hip 10 and the rotation axis 12 of the ankle 14.

Known posterior strut AFOs include a posterior strut 16 that is generally positioned perpendicular to the longitudinal axis 4 of the foot 2 or parallel to the rotation axes 6 of the patient's knee 8 and/or hip 10. This positioning of the posterior strut 16 on the AFO tends to urge the longitudinal axis 4 of the patient's foot 2 toward the line of progression 23 and/or the rotation axis 12 of the ankle 14 toward the rotation axes 6 of the patient's knee 8 and/or hip 10, resulting in unnatural and potentially harmful anatomical alignment between the user's ankle and knee and hip.

Rather than positioning the posterior strut perpendicular to the longitudinal axis of the foot, embodiments of the present disclosure generally align the strut(s) of the orthosis with the line of progression 23 or obliquely to the longitudinal axis 4 (shown in FIG. 3) of the patient's foot on the footplate. For instance, and as seen in FIG. 3, embodiments of the present disclosure can align at least a connecting portion 18a of a posterior strut 18 generally perpendicular to the line of progression 23. This has the advantage of better maintaining the natural offset or misalignment between the rotation axis of the user's ankles, and the rotation axes of the user's knees and hips. It also encourages the user to walk more normally and comfortably rather than creating a forced and unnatural anatomical alignment as in the prior art.

Referring again to FIG. 2, the footplate 5 is arranged obliquely to at least the connecting portion 9a of the posterior strut 9 to accommodate external rotation of the user's foot during gait. For instance, the connecting portion 9a of the posterior strut 9 can be generally normal to or in line with the line of progression 23 while the longitudinal axis of the footplate 5 is externally rotated between about 5 and about 7 degrees relative to the line of progression 23. This can beneficially encourage users to walk normally or more naturally, taking pressure off of other joints, such as the knees and hips. It also decreases the likelihood of foot and/or leg fatigue because the orthosis 3 more naturally moves with the user's foot during gait rather than conflicting with it.

In addition, this can also make the user feel more normal wearing the orthosis 3, resulting in greater confidence and as a result increased compliance. Further, because the orthosis 3 encourages users to walk more naturally, the orthosis 3 can be used in the rehabilitation of an injury and may also provide additional stability for patients with other instabilities, such as ankle instabilities.

In other embodiments, the footplate 5 can be arranged obliquely to at least the connecting portion 9a of the posterior strut 9 to accommodate any amount and direction of foot rotation or center of pressure during gait deemed appropriate by a clinician. For instance, the connecting portion 9a of the posterior strut 9 can be generally in line with the line of progression 23 while the longitudinal axis of the footplate 5 is externally rotated about 3 degrees, about 4 degrees, about 5 degrees, about 6 degrees, about 7 degrees, about 8 degrees, or about 9 degrees relative to the line of progression 23. In other embodiments, the longitudinal axis of the footplate 5 is externally rotated between about 2 degrees and about 18 degrees, about 4 degrees and about 12 degrees, or about 5 degrees and about 10 degrees relative to the line of progression 23. It will be appreciated that in other embodiments the longitudinal axis of the footplate can be externally rotated more or less relative to the line of progression.

In addition to the rotational offset between the footplate 5 and the posterior strut 9, the orthosis 3 is arranged to allow a user to experience a more comfortable and natural gait by accommodating voluntary movement of the foot and resisting or limiting involuntary plantarflexion of the user's foot.

Figure 3B:
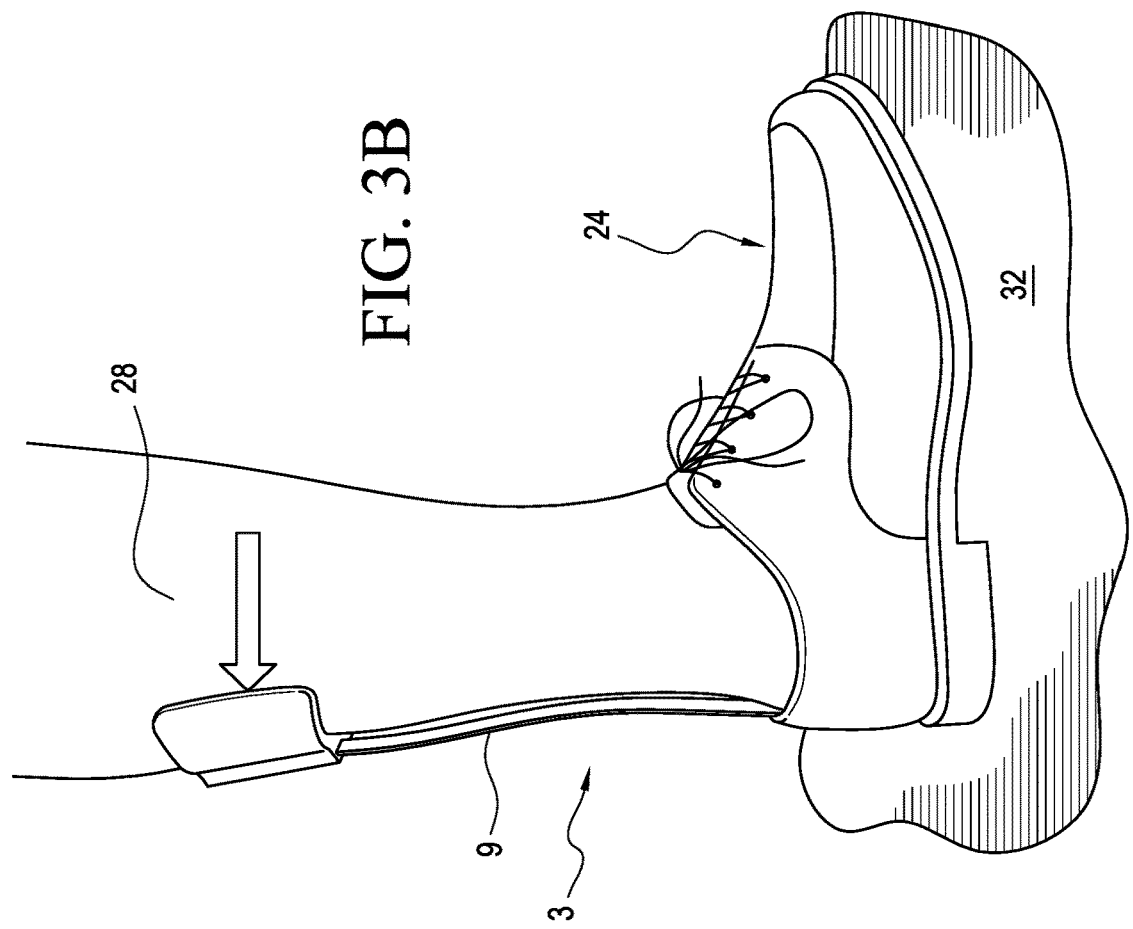
FIG. 3B is a side view of the system in FIG. 1 in use according to an embodiment.
Figure 3A:
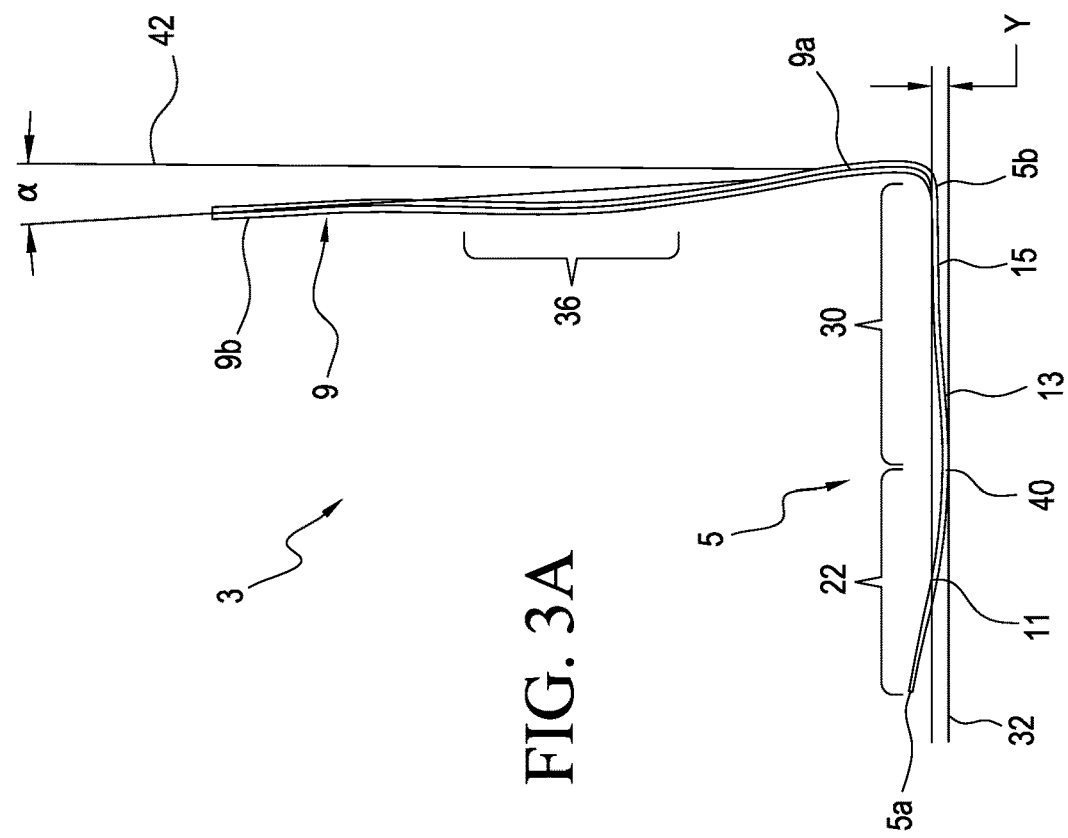
FIG. 3A is a side view of the system in FIG. 1.

Referring to FIGS. 3A and 3B, the orthosis 3 can maintain the user's foot in a neutral or near-neutral position during the swing phase. This beneficially helps to reduce the likelihood of the foot dragging or catching during the swing phase. It also reduces or eliminates the need for a user to lift or swing the hip (also referred to as hip hiking) during gait.

According to a variation, the forefoot portion 11 of the footplate 5 is inclined or curved in a proximal or upward direction from the midfoot portion 13. This can allow the footplate 5 to rock or rotate forward onto the forefoot portion 11 when the heel portion 15 is rotated upward away from the ground 32. As such, when the footplate 5 is positioned in a shoe 24 (shown in FIG. 3B) or other footwear having a heel lift of a distance Y, the posterior strut 9 forms an acute angle α relative to a perpendicular line 42 extending from the ground 32 or other support surface under the shoe 24. This in effect can position the proximal end portion 9b of the posterior strut 9 anterior of the heel end 5b of the footplate 5, advantageously helping the orthosis 3 to maintain or hold the user's foot in a neutral or slightly dorsiflexed position during the swing phase of the gait cycle.

For instance, when the footplate 5 is positioned in a shoe 24 with a heel lift Y of about 8 mm, the posterior strut 9 can be at an acute angle α of about 5 degrees. In an embodiment, an increase of about 4 mm in the heel lift Y, increases the acute angle α by about 2 degrees. When the footplate 5 of the orthosis 3 is placed in a shoe 24 defining a heel lift Y of about 12 mm, the posterior strut 9 can be at an acute angle α of about 7 degrees. When the footplate 5 of the orthosis 3 is placed flat on the ground 32, the posterior strut 9 can be at an angle α of zero or near-zero degrees. It will be appreciated that the angle between the posterior strut 9 and footplate 5 may vary. Optionally, the angle between the posterior strut 9 and the footplate 5 is generally constant in different sizes of the orthosis 3, making the orthosis 3 more versatile and adapted to fit users with differently sized calves and/or feet. This is beneficial over prior art AFOs forming posterior strut angles that vary by size of the AFO even through there is no established correlation between users' calf sizes and foot sizes.

In addition, soft tissue or muscle on the posterior aspect of a user's lower leg 28 can help the orthosis 3 to dorsiflex the user's foot as seen in FIG. 3B. During swing phase, the lower leg 28 pushes the posterior strut 9 in a posterior direction, which, in turn, rotates or forces the footplate 5 upward against the bottom surface of the user's foot, biasing the foot toward a dorsiflexed position. This advantageously helps prevent the foot from dragging or catching during the swing phase. The raised position of the forefoot portion 11 of the footplate 5 may also help to raise the toes of the user during the swing phase.

The orthosis 3 also resists or limits involuntary flexion of the footplate 5. To help resist involuntary plantarflexion, the footplate 5 defines a supportive zone 30 of increased rigidity. The supportive zone 30 can be located between the forefoot portion 11 and the heel end 5*b* of the footplate 5 and arranged is extend below a center of mass of the user's foot on the footplate 5. For instance, the supportive zone 30 can correspond to between about 0.3 and about 0.6, or about 0.4 and about 0.5 (e.g., about 0.43) of a total length of the footplate 5 from the heel end 5*b* of the footplate 5.

The supportive zone 30 is generally more rigid than other portions of the footplate 5. This greater rigidity can be achieved at least by increasing the thickness of one or more portions of the footplate 5 through the supportive zone 30. Conversely, greater flexibility of the footplate 5 can be achieved at least by decreasing the thickness at certain portions of the footplate 5. For instance, a thickness of the supportive zone 30 along the midfoot portion 13 can be between about 0.5 and about 1, or about 0.6 and about 0.8 (e.g., about 0.7) times a thickness of the supportive zone 30 along the heel portion 15. According to an embodiment, the thickness of the supportive zone 30 along the midfoot portion 13 can be between about 1.8 mm and about 2.8 mm (e.g., about 2.2 mm), and the thickness of the footplate 5 in the heel portion 15 can be between 2.4 mm and about 3.8 mm (e.g., about 3.0 mm). The thickness of the footplate 5 is generally defined between top and bottom surfaces of the footplate 5.

In an embodiment, a thickness of the supportive zone 30 along the midfoot portion 13 can be between about 1.5 and about 3.5, or about 2.0 and about 3.0 (e.g., about 2.4) times a thickness of the forefoot portion 11. In other embodiments, a thickness of the supportive zone 30 along the heel portion 15 can be between about 2.0 and about 5.0, or about 3.0 and about 4.0 (e.g., about 3.3) times a thickness of the forefoot portion 11.

The increased thickness of the footplate 5 through the supportive zone 30 provides enhanced rigidity to where the footplate 5 supports most of the user's foot weight, beneficially helping to resist involuntary plantarflexion. In other words, the enhanced rigidity of the footplate 5 through the supportive zone 30 at least in part supports the weight of the foot so that the footplate 5 does not undesirably drop or sag when the foot is positioned on the footplate 5. In an embodiment, the combination of the supportive zone 30 of the footplate 5 and structure of the posterior strut 9 described below can be arranged to resist involuntary plantarflexion of the user's foot, at a minimum force of about 8 N (e.g., about 1.8 lbf) when the foot is plantar flexed at an angle of about 10 degrees. This minimum force value is generally representative of unsupported foot weight and the angle of about 10 degrees is generally representative of about 5 degrees of dorsiflexion provided by the orthosis 3, with an additional 5 degrees of allowable plantarflexion of the footplate 5 described below. Dorsiflexion means flexion of the foot in an upward or proximal direction. Plantarflexion means movement of the foot in which the foot or toes flex downward toward the bottom of the foot. It will be appreciated that the thickness of the footplate 5 in the supportive zone 30, the heel portion 15, and the midfoot portion 13 can be more or less relative to the forefoot portion 11 and/or one another.

The footplate 5 can also accommodate voluntary dorsiflexion of a user's foot. For instance, a first deflection zone 22 can be defined along a length of the footplate 5 anterior of the heel portion 15 such that the footplate 5 deflects or flexes through the first deflection zone 22 during gait. When a user's foot moves from mid stance through toe-off, the loading of the footplate 5 causes the footplate 5 to bend or flex through the first deflection zone 22. This allows the forefoot portion 11 of the footplate 5 to deflect in a dorsal or upward direction under the toes of the user, moving the footplate 5 toward dorsiflexion. The flexibility of the forefoot portion 11 also helps prevent or limit the footplate 5 from forcing the toes of the user into the top of a shoe or boot during gait. It also advantageously limits or prevents lateral pivoting of the user's foot during gait. Such lateral pivoting is commonly known as heel whip and can result in excessive torque on the knee and pain over time.

According to a variation, the first deflection zone 22 is defined at least in part by a portion of the forefoot portion 11 that is thinner than a length of the midfoot and/or heel portions 13, 15. In an embodiment, a thickness of the first deflection zone 22 along the forefoot portion 11 can be between about 0.1 and about 0.7, about 0.2 and about 0.6, or about 0.3 and about 0.5 (e.g., about 0.3) times a thickness of the footplate 5 along the heel portion 15. A thickness of the first deflection zone 22 along the forefoot portion 11 can be less than about 0.5, about 0.4, about 0.35, or about 0.3 times a thickness of the footplate 5 along the heel portion 15. A thickness of the first deflection zone 22 along the forefoot portion 11 can be between about 0.5 mm and about 1.5 mm (e.g., about 0.9 mm) and a thickness of the footplate 5 along the heel portion 15 can be between about 1.5 mm and about 5 mm (e.g., about 3.0 mm).

In an embodiment, a thickness of the first deflection zone 22 along the forefoot portion 11 can be between about 0.2 and about 0.7, or about 0.3 and about 0.6 (e.g., about 0.4) times a thickness of the footplate 5 along the midfoot portion 13. A thickness of the first deflection zone 22 along the forefoot portion 11 can be less than about 0.6, about 0.5, about 0.45, or about 0.4 times a thickness of the footplate 5 along the midfoot portion 13. A thickness of the first deflection zone 22 along the forefoot portion 11 can be between about 0.7 mm and about 1.1 mm (e.g., about 0.9 mm) and a thickness of the footplate 5 along the midfoot portion 13 can be between about 1.8 mm and about 2.5 mm (e.g., about 2.2 mm). The thinner configuration of the footplate 5 through the first deflection zone 22 also reduces the overall profile of the orthosis 3 and allows the footplate 5 to be more easily positioned in footwear such as a shoe. The flexibility of the footplate 5 through the first deflection zone 22 also helps prevent or limit upward force on the user's toes when wearing a shoe.

As described in more detail below, the flexibility of the footplate 5 through the first deflection zone 22 can also be defined at least in part by a layered or laminate structure of the footplate 5. In an embodiment, the structure of the footplate 5 through the first deflection zone 22 can include top and bottom layers comprising a fiberglass composite weave, and one or more layers comprising unidirectional carbon fiber composite located between the top and bottom layers. The layers of fiberglass are more flexible than the one or layers of carbon fiber, providing greater flexibility through the first deflection zone 22.

According to a variation, a thickness of the footplate 5 is variable to direct flexing or deflection of the footplate 5 toward the first deflection zone 22. For instance, the footplate 5 can define an overall length between the toe end 5*a* and the heel end 5*b* of the footplate. Between about 40% and about 60% of the overall length of the footplate 5 from the heel end 5*b*, the thickness of the footplate 5 can be less than about 0.75 of a maximum thickness of the footplate between the heel end 5b and and about 40% of the overall length of the footplate 5. Between about 60% and about 80% of the overall length of the footplate 5 from the heel end 5b, the thickness of the footplate 5 can be less than about 0.55 of the maximum thickness of the footplate 5 between the heel end 5b and about 40% of the overall length of the footplate 5. Between about 80% and about 100% of the overall length of the footplate 5 from the heel end 5b, the thickness of the footplate 5 can be less than about 0.35 of the maximum thickness of the footplate 5 between the heel end 5b and about 40% of the overall length of the footplate 5.

According to a variation, a thickness of the forefoot portion 11 through the first deflection zone 22 tapers to direct flexing or deflection of the footplate 5 to under the ball or heads of the metatarsal bones of the user's foot. For instance, the thickness of the forefoot portion 11 can taper from a transition point 40 where the footplate 5 angles or curves upwardly from in the mid-foot portion 13 toward the toe end 5a of the footplate 5. In an embodiment, from the toe end 5a to about 0.2 the overall length of the footplate 5, the forefoot portion 11 can have a thickness of about 0.9 mm. From about 0.2 of the overall length of the footplate 5 to about 0.4 of the overall length of the footplate 5 from the toe end 5a, the forefoot portion 11 can have a thickness of about 1.6 mm. From the toe end 5a to between about 0.2 or about 0.4 the overall length of the footplate 5, a thickness of the forefoot portion 11 can vary greater than about 35%, about 40%, about 45%, or about 50% (e.g., about 44%).

This helps ensure that at the anterior aspect of the supportive zone 30, the flexibility of the forefoot portion 11 can accommodate flexion. In an embodiment, a thickness of the footplate 5 at about 0.4 of the overall length of the footplate 5 from the toe end 5a is about 1.6 mm and decreases to about 0.9 mm at the toe end 5a of the footplate 5. It will be appreciated that in other embodiments, the thickness of the footplate 5 can vary differently.

The overall support provided by the orthosis 3 can also be influenced by the rigidity or stiffness of the posterior strut 9. For instance, the posterior strut 9 can include a length having a rigidity adapted so that the orthosis 3 resists or limits involuntary plantarflexion. More specifically, a length of the posterior strut 9 has a rigidity arranged so that the footplate 5 does not undesirably drop or sag when weight is applied to the footplate 5. However, the posterior strut 9 also defines a second deflection zone described below that facilitates voluntary plantarflexion of the footplate 5.

This arrangement further advantageously allows users to experience common activities, like driving a car or riding a bicycle, where plantarflexion is necessary. Moreover, if an AFO does not sufficiently accommodate plantarflexion, users can have an abrupt heel strike, with minimal cushioning. This can cause users to experience knee pain from the tibia being driven anterior of the knee axis as the transition from heel strike to loading response occurs more quickly than normal. In some circumstances, this can even result in injury to the ligaments of the knee.

To help accommodate voluntary plantarflexion of a user's foot, a second deflection zone 36 is defined along a length of the posterior strut 9 such that the posterior stmt 9 controllably deflects or flexes through the second deflection zone 36. When a user moves the foot toward plantarflexion, the downward force on the footplate 5 causes the posterior strut 9 to bend or flex through the second deflection zone 36. This in turn allows at least the forefoot portion 11 and/or the midfoot portion 13 of the footplate 5 to rotate downwardly toward the bottom of the footplate 5, moving the orthosis 3 toward plantarflexion.

The second deflection zone 36 can extend along a partial length of the posterior stmt 9. In an embodiment, the second deflection zone 36 can extend along between about 20% and about 80%, about 30% and about 70%, or about 40% and about 60% (e.g., about 50%) of the overall length of the posterior strut 9. The location and/or amount the posterior strut 9 flexes through the second deflection zone 36 can be controlled by varying the thickness of the posterior strut 9 and/or by changing the cross-sectional area or shape of the posterior strut 9 in the second deflection zone 36. For instance, the second deflection zone 36 can be located between the connecting portion 9a and the proximal end portion 9b and a width of the posterior strut 9 through the second deflection zone 36 can be narrowed to increase flexibility. It will be appreciated that the second deflection zone 36 can include a single or multiple distinct regions along the length of the posterior strut 9.

According to a variation, as the user's shoe or footwear does not typically flex at the heel and the rotation axis 12 of the ankle (shown in FIG. 3) is proximal to the heel portion 11, the connecting portion 9a of the posterior strut 9 is arranged to be generally rigid and the second deflection zone 36 is located proximal to the connecting portion 9a. The posterior strut 9 can be arranged to be rigid or substantially rigid from the footplate 5 up to between about 25% and about 35% (e.g. about 30%) of the overall length of the posterior strut 9 from the footplate 5 to help ensure that the posterior strut 9 does not flex over the heel of the user.

The rigidity of the posterior strut 9 can also be customized by varying the thickness of the posterior strut 9 beyond the second deflection zone 36 and/or by changing the cross-sectional area or shape of the posterior strut 9 in areas of desired stiffness. For example, the connecting portion 9a can include a curve or curved cross section across a width of the connecting portion 9a. This enhances the comfort and fit of the orthosis 3, as well as creates a more rigid section of the posterior strut 9 at or near the heel, which resists flexing during use. This beneficially limits undesired flexing at the heel during use, which, in turn, helps prevent the posterior strut 9 from impinging on or injuring the heel during use of the orthosis 3. Excessive flexing of the posterior strut 9 in the connecting portion 9a can apply pressure to the heel bone or to the attachment of the Achilles tendon to the heel bone, during gait, and more specifically during periods of dorsiflexion, resulting in pressure points and discomfort. In an embodiment, the orthosis 3 can provide an average resistance of about 14 N (e.g., about 3.2 lbf) when the user's foot is plantar flexed at an angle of 10 degrees.

In addition, the proximal end portion 9b of the posterior strut 9 can be arranged to be inserted in a mating cuff or base element, which may result in this portion of the posterior strut 9 having an increased rigidity. The second deflection zone 36 of the posterior strut 9 can thus be arranged to flex between the connecting portion 9a and the proximal end portion 9b. Furthermore, the proximal end portion 9b of the posterior strut 9 can also incorporate a curvature to increase rigidity in this area to limit undesirable flexing that occurs between the interface of the posterior strut 9 and the base element.

The combination of deflection and supportive zones defined by the orthosis 3 thus work together to generate more natural movements of the footplate 5 and posterior stmt 9 during use, allowing a user of the orthosis 3 to experience a more comfortable gait and prevent or limit undesirable toe dragging and painful pressure points.

According to a variation, the footplate 5 can include a layered structure of two or more discrete structural layers. Each layer can extend along at least a segment of a length of the footplate 5 wherein different regions are defined having different thicknesses and stiffness.

The length and/or thickness of the layers may be varied according to a desired stiffness in designated areas. The stiffness of the footplate 5 can also be varied using different materials. For example, unidirectional carbon fiber is stiffer than E-glass but has lower torsional stiffness than woven carbon fiber. As such, E-glass material can be included in an area of the footplate 5 where some flexibility is desirable (e.g., the forefoot portion) and other areas of the footplate 5 can include carbon fiber where additional structural support is needed. Greater stiffness of the footplate 5 can be achieved at least by increasing the amount or thicknesses of layers. Conversely, greater elasticity is obtained at least in part in portions of the footplate having fewer or thinner layers. According to a variation, the footplate 5 can be configured as disclosed in U.S. Pat. No. 7,266,910, the disclosure of which is incorporated by reference and belongs to the assignee of this disclosure.

In an embodiment, the footplate 5 can increase in stiffness along a defined or desired rotation position relative to a line of progression (e.g. about 5 to 7 degrees of external rotation). For instance, the thicknesses of each of the layers may be individually increased or decreased in order to obtain such an increasing stiffness. Since the thickness of different layers can be used to change the flexibility or elasticity of the footplate 5, and thereby the stiffness, the edges of one or more of the layers at the toe and heel portions 11, 15 can be generally linear and perpendicular to the line of progression 23. For example, by arranging an edge thickness that is substantially perpendicular to the line of progression 23, it can enable easier control of the flexibility of the footplate 5. It has been found that when the edges are not perpendicular to the line of progression, it is difficult to control the elasticity of the footplate 5 since non uniform edges, such as those that are concave or convex shaped, have a tendency to generate a stiffness gradient across the length thereof. It will be understood, however, that the embodiments described herein may have layers with edges orientated relative to the line of progression that are concave, convex, stepwise, linear, serrated, and combinations thereof if a stiffness gradient across the width of the footplate is desired.

The distance between borders where the thickness between two or more layers is different can determine at least partly the flexibility of the footplate 5 in a way that the flexibility is more continuous when the distance is short or discontinuous when the distance is increased.

According to a variation, the posterior strut 9 and the footplate 5 can be customized to a specific line of progression. This beneficially allows the orthosis 3 to be customized to a patient having abnormal gait dynamics or used comfortably and confidently by patients with anatomical deformities. By way of example, the layers can have different shapes to soften or make the footplate 5 more flexible along a corrected line of progression or a desired center of pressure path. The footplate 5 may be canted along different portions of the line of progression.

In other embodiments, the footplate 5 can offer a varying stiffness to encourage or accommodate a specific foot rotation relative to the line of progression. For instance, the footplate 5 can be stiffened along the medial and/or lateral sides 17, 19. This beneficially can enhance stability and/or encourage patients to follow a specific or corrected center of pressure path, such as one externally rotated during gait. This arrangement may further provide patients with inversion or eversion control for those who are prone to ankle instability.

The footplate 5 can be formed of any suitable material. For instance, the footplate 5 can include one or more rigid plastic materials, such as synthetic polymers ("Nylon"), polycarbonates, Acrylonitrile-Butadiene-Styrene ("ABS") materials, fiber filled rigid plastic materials, combinations thereof, or the like. Alternatively, the footplate may include polypropylene, polyurethane or polyethylene. The footplate 5 can be molded.

In other embodiments, the footplate 5 can be formed of carbon fibers. The carbon fibers can be impregnated with a thermoplastic material, such as polypropylene or nylon, or a resin. Alternatively, other structural materials may be used alone or in combination with carbon fibers. Such other structural materials include Kevlar aramid fibers, glass fibers or combinations thereof. The fibers can be impregnated with an epoxy resin or other suitable resin system. The footplate can include layers bonded together using methods known to those skilled in the art. In other embodiments, the footplate 5 can include one or more polymeric layers molded over one or more carbon layers.

According to a variation, at least some of the layers may be unidirectional fibers that are oriented in generally a single direction running substantially parallel to the line of progression 23. The orientation of these fibers is provided to maintain a large stiffness in a walking direction and to thereby minimize the thickness of the layer. Alternatively, the fibers may be arranged in different orientations relative to the line of progression 23. This beneficially can help limit twisting during use.

According to a variation, the stiffness of the posterior strut 9 can vary. For instance, the connecting portion 9a of the posterior strut 9 can include a varying thickness to vary its stiffness. In other embodiments, the posterior strut 9 can have varying material alignment to vary its stiffness. In other embodiments, the posterior strut 9 can include a curved cross-section to provide additional stiffness at the heel, as a curved cross-section is stronger than a flat cross-section.

FIGS. 4-7 show an orthotic system comprising an orthosis 25 according to another embodiment. The orthosis 25 can include a footplate 27 and a leg support 29 extending upwardly from the heel portion of the footplate 27. The leg support 29 includes a posterior strut 31 arranged to extend along the posterior aspect of the user's lower leg. The footplate 27 and the leg support 29 can be substantially formed as a single unit and constructed similarly to the previously described embodiments. The orthosis 25 further includes a securing device 33 for extending circumferentially around a user's leg (not shown) described in additional detail below.

Figure 5:
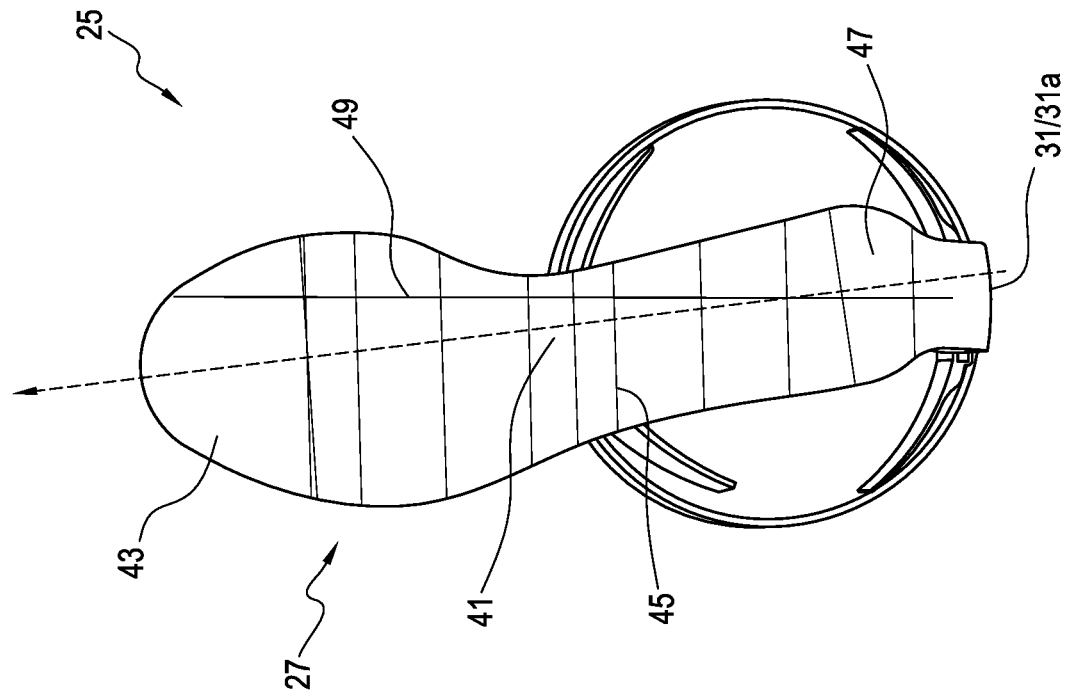
FIG. 5 is a bottom view of the system in FIG. 4.
Figure 4:
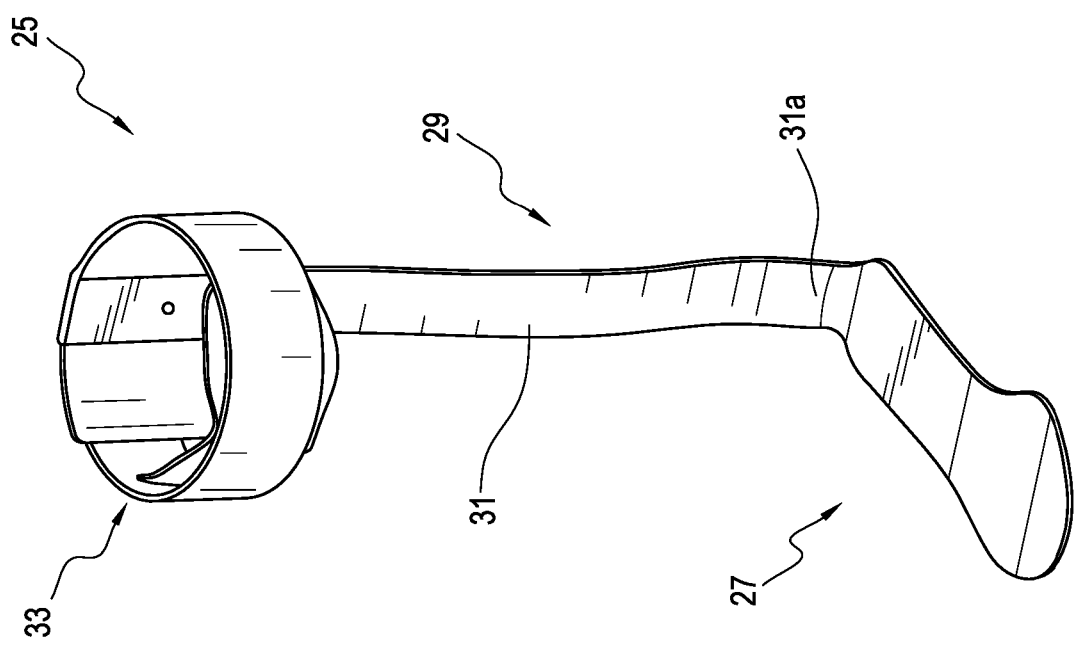
FIG. 4 is a perspective view of an orthopedic system according to another embodiment.

As seen in FIG. 5, the footplate 27 defines a longitudinal axis 41, a forefoot portion 43, a midfoot portion 45, a heel portion 47, and a line of progression 49 extending from the heel portion 47 to the midfoot portion 45 to the forefoot portion 43.

The posterior strut 31 can be connected to the footplate 27 via a connecting portion 31a of the posterior strut 31. Similar to the previously described embodiments, the footplate 27 can be arranged obliquely to at least the connecting portion 31a to accommodate external rotation of the user's foot during gait. For instance, the connecting portion 31a of the posterior strut 31 can be substantially normal to the line of progression 49 while the longitudinal axis of the footplate 27 is externally rotated about 5-7 degrees relative to the line of progression 49. This beneficially can encourage users to walk normally, taking pressure off of other joints, such as the knees and hips. In other embodiments, the footplate 27 can be arranged obliquely to the connecting portion 31a of the posterior strut 31 to accommodate any amount and direction of foot rotation or center of pressure during gait deemed appropriate by a clinician. In other embodiments, the footplate 27 can be arranged to encourage users into a corrected line of progression.

Referring now to FIG. 6, the connecting portion 31a can include a transition portion 51 between the heel portion 47 of the footplate 27 and the posterior strut 31. The transition portion 51 can have an increased radius. This beneficially can help increase the strength of the orthosis 25 at the transition portion 51 and improve its fatigue performance.

The connecting portion 31a is shown being integral to the posterior strut 31 and the footplate 27 however in other embodiments the connecting portion can comprise a separate member 31b connecting the posterior strut 31 and the footplate 27 as seen in FIGS. 6A and 6B. The separate connecting portion 31b can form a joint between the posterior strut 31 and the footplate 27. The separate connecting portion 31b can be attached to the posterior strut 31 and the footplate 27 in any suitable manner. For instance, the connecting portion 31b can be overmolded on a distal end of the posterior stmt 31 and on the heel portion 47 of the footplate 27. In other embodiments, the separate connecting portion 31b can be attached to the posterior strut 31 and/or the footplate 27 via one or more mechanical fasteners and/or adhesives.

The connecting portion 31b can be formed from a plastic material, a polypropylene composite, or any other suitable material. The connecting portion 31b can be formed of a plastic material having a tough or durable configuration. The connecting portion 31b can be heat moldable. The connecting portion 31b can be custom molded to a specific user's anatomy.

The connecting portion 31b can include an upper area 52 defining a first opening 56 receiving the posterior strut 31, a lower area 54 defining a second opening 58 receiving the heel portion 47, and a transition 51b curving between the upper and lower areas 52, 54. The connecting portion 31b can be more rigid than the posterior strut 31, limiting flexing of the orthosis 25 at the heel during use. A separate connecting portion between the footplate 27 and the posterior strut 31 can also help avoid internal stress concentrations commonly found in an integral transition or joint between a footplate and a posterior strut, improving the durability of the AFO. In other embodiments, the connecting portion can be integral to one of the footplate 27 and the posterior strut 31 but not the other.

FIGS. 7 and 7A show the transition portion 51 in greater detail. The shape of the transition portion 51 may be determined by the shape of a shoe such that it will fit snugly inside the shoe and but will not excessively rub against the shoe or a user's heel.

The transition portion 51 can include a curve or curved profile 53 across a width of its inner surface. This enhances the comfort and fit of the orthosis 25, as well as creates a more rigid section of the posterior strut 31 at or near the heel, which resists flexing during use. For instance, the curved profile 53 advantageously can better accommodate patient anatomies, specifically the curvature of the heel, compared to a linear profile as found in the prior art. As such, the orthosis 25 provides a more comfortable fit to a user. According to a variation, the curved profile 53 can include a varying curvature across its width or curved and linear portions.

The curved profile 53 further provides additional stiffness to the posterior strut 31 at or near the heal area, resulting in a more rigid orthosis below the ankle joint. This beneficially limits undesired flexing of the posterior strut 31 at the heel during use, which, in turn, helps prevent the posterior strut 31 from impinging on or injuring the heel during use of the orthosis 25.

Optionally, the curved profile 53 can transition to a linear or generally rectangular profile at a location above the heel of the user, increasing the flexibility of the posterior strut 31 in the area above heel such as over the Achilles tendon. This allows the posterior strut 31 to flex more over the Achilles tendon, improving user comfort, while limiting flexing at the heel during use, which helps prevent the posterior strut 31 from impinging on or injuring the heel during use of the orthosis 25.

In other embodiments, the transition portion 51 can have a greater width and/or thickness in the area of the heel, increasing its stiffness and reducing the likelihood of the posterior strut 31 impinging on the heel.

The transition portion 51 can also include a curve or curved profile 55 across a width of its outer surface. The curved profile 55 can generally correspond to the heel portion inside of a patient's shoe. This beneficially improves the fit of the orthosis 25 within the shoe as compared to known struts that tend to push the user's foot anterior in the shoe resulting in discomfort and in some cases, the need to buy alternative footwear in a larger size. This can also make the user feel more normal wearing the orthosis 25 resulting in greater confidence and as a result increased compliance.

Figure 9:
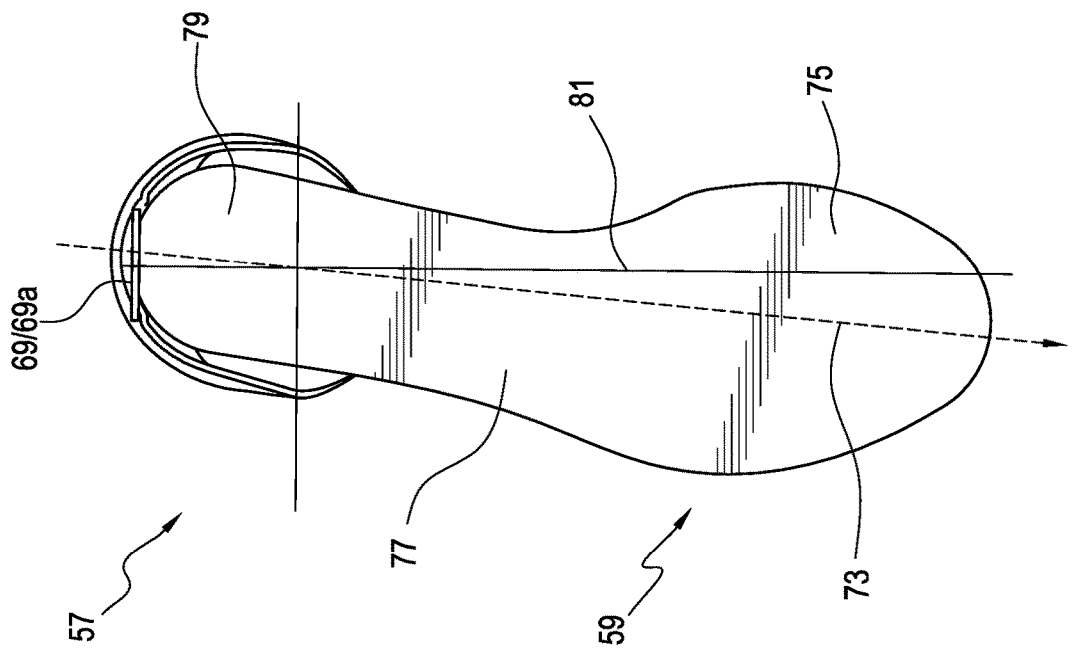
FIG. 9 is a top view of the system in FIG. 8.
Figure 8:
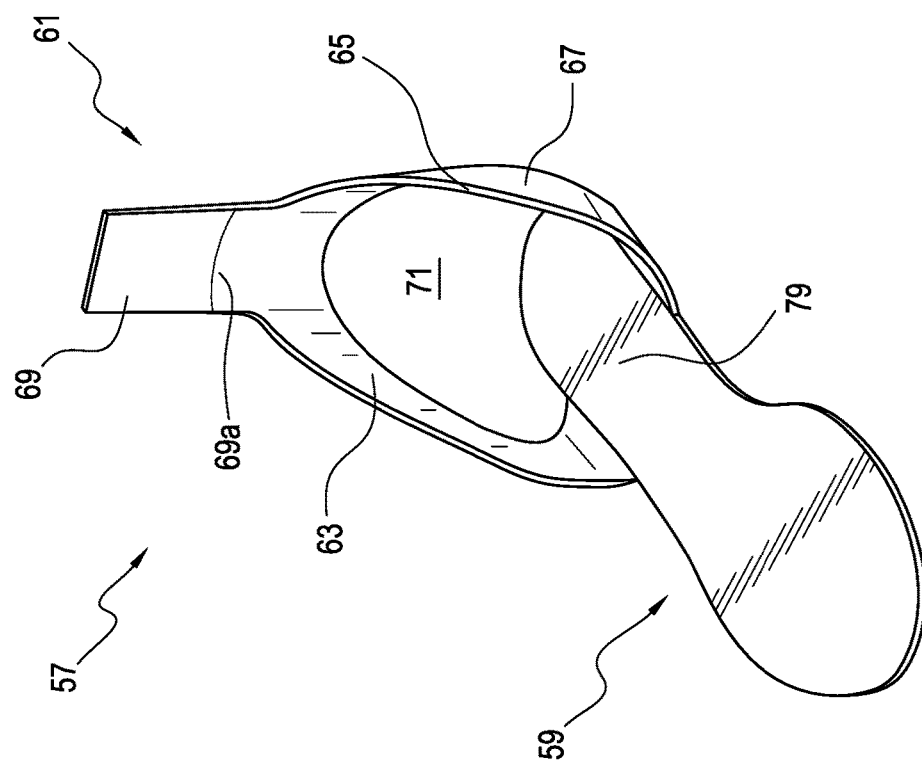
FIG. 8 is a perspective view of an orthotic system according to another embodiment.

FIGS. 8 and 9 show an orthotic system comprising an orthosis 57 according to yet another embodiment. The orthosis 57 is an AFO arranged to assist the biomechanics of the foot, ankle, and lower leg. The orthosis 57 includes a footplate 59 and a leg support 61 extending upwardly from the heel portion 79 of the footplate 59. The footplate 59 and the leg support 61 can be substantially formed as a single unit. The leg support 61 can be separate from and attached to the footplate 59. It should be appreciated that the orthosis 57 can be constructed similarly to the previously described embodiments.

As seen, the leg support 61 can include a lower lateral strut 63 connected to the lateral side of the footplate 59 and a lower medial strut 67 connected to the medial side of the footplate 59. The lower lateral and medial struts 63, 67 generally extend upwardly and wrap or curve inwardly around the user's ankle area to a location where they come together to form an upper posterior strut 69 above the heel area of a user and arranged to extend along the posterior aspect of the user's lower leg or calf. According to a variation, the lateral and medial struts 63, 67 can be curved to generally correspond to the shape of the user's foot, improving comfort for a user and the fit of the orthosis 57 within a shoe. In other embodiments, the upper posterior strut 69 can be shaped to generally correspond to the shape of the user's lower leg.

At least one of the lower lateral and medial struts 63, 67 can include a curved cross section or can be rounded or rolled along the edges 65 to enhance comfort and add structural rigidity in the heel area region. Optionally, the lower lateral and medial struts 63, 67 can be rolled along the edges in the opposite direction, further increasing rigidity.

The lower lateral and medial struts 63, 67 at least in part define an opening 71 sized and configured to receive and accommodate the user's heel. This beneficially provides a more comfortable fit and prevents the leg support 61 from impinging on or injuring the heel during use. Further, the combination of the upper posterior strut 69 and the lower lateral and medial struts can offer increased stiffness and/or medial or lateral support and stability. The footplate 59 defines a longitudinal axis 73, a forefoot portion 75, a midfoot portion 77, a heel portion 79, and a line of progression 81 extending from the heel portion 79 to the midfoot portion 77 to the forefoot portion 75.

Similar to the previously described embodiments, the footplate 59 can be arranged obliquely to the leg support 61 to help accommodate external rotation of the user's foot during gait. For example, a connecting portion 69*a* of the upper posterior strut 69 can be generally normal to the line of progression 81 while the longitudinal axis of the footplate 59 is externally rotated between about 5 and about 7 degrees relative to the line of progression 81. In other embodiments, the longitudinal axis of the footplate 59 can be arranged obliquely to the leg support 61 to accommodate any amount and direction of foot rotation or center of pressure during gait deemed appropriate by a clinician. This beneficially can encourage users to walk normally, taking pressure off of other joints, such as the knees and hips. It also can help encourage users into a corrected line of progression.

Figure 11:
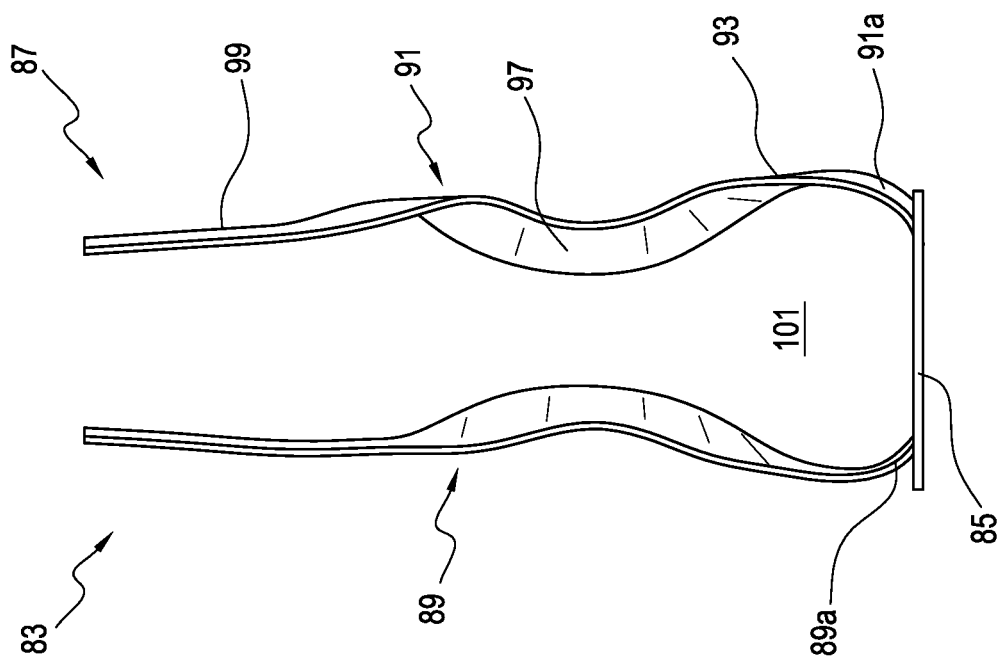
FIG. 11 is a front view of the system in FIG. 10.
Figure 10:
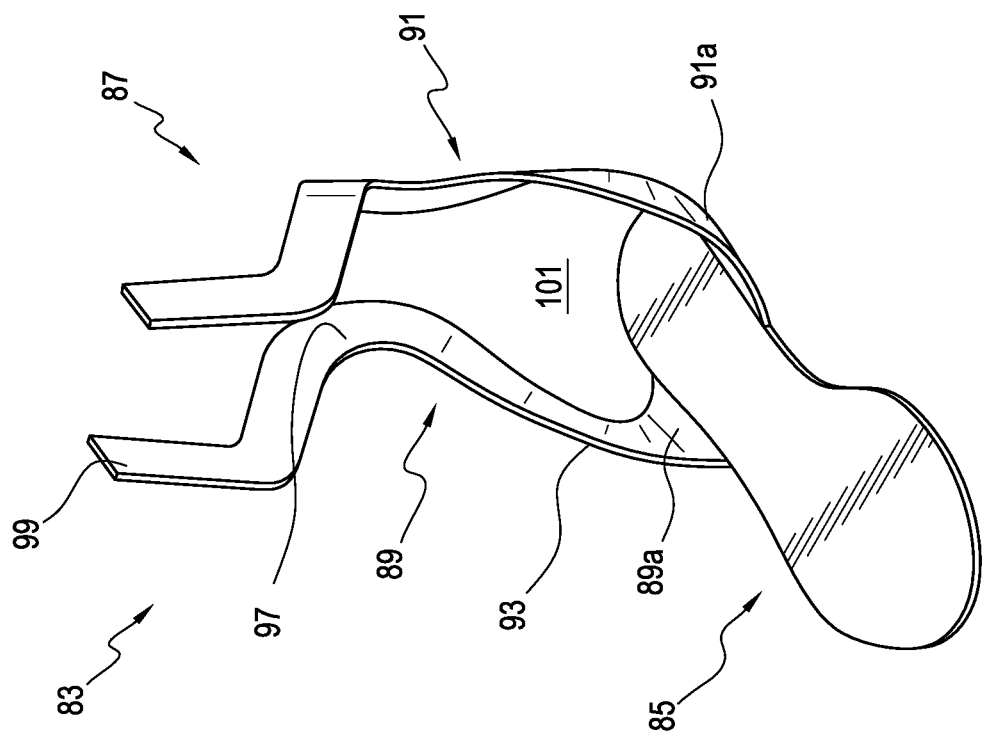
FIG. 10 is a perspective view of an orthotic system according to another embodiment.

FIGS. 10 and 11 show an orthotic system comprising an orthosis 83 according to yet another embodiment. The orthosis 83 is arranged to assist the biomechanics of the foot, ankle, and lower leg. The orthosis 83 includes a footplate 85 and a leg support 87 extending upwardly from the footplate 85. The footplate 85 and the leg support 87 can be substantially formed as a single unit. The leg support 87 can be separate from and attached to the footplate 85. The footplate 85 and the leg support 87 can be constructed similarly to the previously described embodiments.

As seen, the leg support 87 can include a dual strut construction. More particularly, the leg support 87 can include a lateral strut 89 connected to the lateral side of the footplate 85 and a medial strut 91 connected to the medial side of the footplate 85.

The footplate 85 can be arranged obliquely to the leg support 87, allowing the orthosis 83 to accommodate a certain or selected degree of rotation of the user's foot during gait. For instance, connecting portions 89*a*, 91*a* of the lateral and medial struts 89, 91, respectively, can be generally in line with a line of progression while the longitudinal axis of the footplate 85 is externally rotated about 4 degrees, about 5 degrees, about 6 degrees, about 7 degrees, or about 8 degrees relative to the line of progression. This advantageously can encourage users to walk normally or into a corrected line of progression as compared to known dual strut AFOs that have the struts in line with the ankle bones, forcing the user's foot to unnaturally point straight forward.

Each strut 89, 91 defines a plurality of curves arranged and configured to generally correspond to the shape of the user's ankle area and lower leg, providing a more anatomical fit and support to the orthosis 83. For instance, each strut 89, 91 can include a lower portion 93 that curves outwardly, upwardly, and then rearwardly from the footplate 85. The connecting portions 89*a*, 91*a* have a greater width than the lower portions of the struts 89, 91, which in effect increases the stability and/or connection strength between the leg support 87 and the footplate 85.

A midfoot portion 97 extends from the lower portion 93 to form a support structure having an inwardly curved configuration and arranged to engage a posterior aspect of the lower leg, helping to maintain the stability of the leg support 87 during gait. In an embodiment, the midfoot portion 97 can be thinner to allow more flexing through the midfoot portion 97 of the strut. In other embodiments, the midfoot portion 97 can be arranged to extend from the lower portion 93 to about the lateral and/or medial side of the lower leg of the user. An upper portion 99 extends upwardly from the midfoot portion 97 and is arranged to engage and provide medial/lateral support to side portions of the lower leg.

The lateral and medial struts 89, 91 are spaced apart by a gap 101. The gap 101 is sized and configured to receive and accommodate the user's lower leg and heel area. This beneficially provides a more comfortable fit and prevents the leg support 87 from impinging on or injuring the user's heel during use.

According to a variation, at least one of the lateral and medial struts 89, 91 can include a curved cross section or can be rounded or rolled along the edges to enhance comfort and add structural rigidity.

Figure 13:
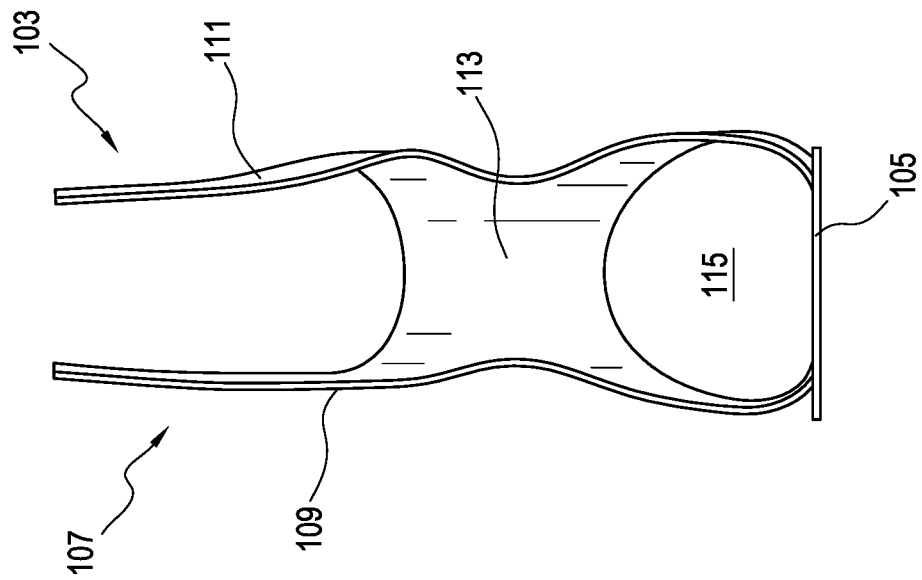
FIG. 13 is a front view of the system in FIG. 12.
Figure 12:
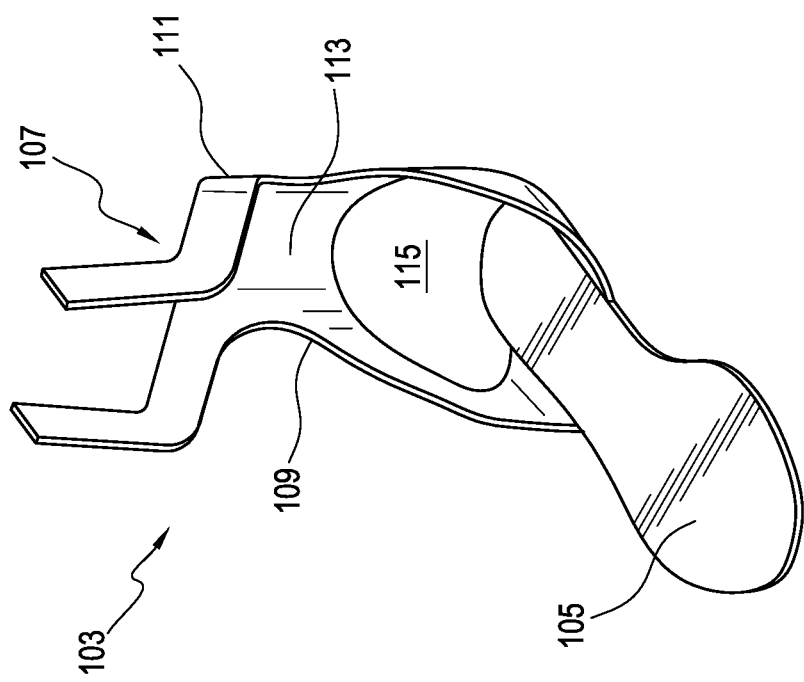
FIG. 12 is a perspective view of an orthotic system according to another embodiment.

FIGS. 12 and 13 show an orthotic system comprising an orthosis 103 according to yet another embodiment. Similar to the other embodiments, the orthosis 103 is arranged to assist the biomechanics of the foot, ankle, and lower leg. For instance, the orthosis 103 includes a footplate 105 and a leg support 107 extending upwardly from the footplate 105. The footplate 105 and the leg support 107 can be constructed similarly to the previously described embodiments.

The leg support 107 can include a dual strut construction similar to the leg support 87 including a lateral strut 109 and a medial strut 111. The primary difference is that the leg support 107 includes a bridge or connecting element 113 connecting the lateral and medial struts 109, 111 above the user's heel. This can offer more stiffness and more medial/lateral support or stability to a user. According to a variation, the connecting element 113 can be removable from the leg support 107. This allows the connecting element 113 to be added for periods when more support is needed (e.g., during activity) and removed when less support is needed. In other embodiments, the connecting element 113 can be interchangeable with other connecting portions exhibiting more or less stiffness, allowing for customization of the leg support 107.

The lateral and medial struts 109, 111 and connecting element 113 define an opening 115 sized and configured to receive and accommodate the user's heel. This beneficially provides a more comfortable fit and prevents the leg support 107 from impinging on or injuring the heel during use.

FIGS. 14-17 show an orthotic system comprising an orthosis 117 according to yet another embodiment. Similar to the other embodiments, the orthosis 117 is arranged to assist the biomechanics of the foot, ankle, and lower leg. The orthosis 117 includes a footplate 119 and a leg support 121 extending upwardly from the heel portion of the footplate 119. The leg support 121 includes a posterior strut 123 arranged to extend along the posterior aspect of the user's lower leg. The footplate 119 and the posterior strut 123 can be substantially formed as a single unit and constructed similarly to the previously described embodiments. For instance, the posterior strut 123 can be connected to the footplate 119 via a connecting portion 123*a* of the posterior strut 123 that is positioned on the footplate 119 so that it is generally perpendicular to the user's line of progression during gait.

The orthosis 117 includes a securing device 125 for extending circumferentially around a user's leg. As seen in FIG. 15, the securing device 125 can include a base element 127 arranged to interface with the posterior strut 123, at least one strap member 129 attached to the base element 127 and arranged to extend and be selectively secured around the user's lower leg, and an anterior shell 131 disposed on an inner surface of the strap member 129. As described in more detail below, the anterior shell 131 can be configured to float or move relative to the posterior strut.

The at least one strap member 129 is a fabric strap attached to the base element 127 with hook and loop fasteners. It will be appreciated however that the at least one strap member 129 can exhibit any suitable configuration and can be attached to the base element 127 in any suitable manner. In an embodiment, the at least one strap member 129 can comprise a first strap member attached to the base element 127 and the anterior shell 131 on the medial side of the leg and a second strap member attached to the base element 127 and the anterior shell 131 on the lateral side of the leg. This has the advantage of providing a better or more balanced transfer of energy between the anterior shell and the posterior strut during gait. The base element 127 can be separate from or integral to the posterior strut 123.

Using the strap member 129 to connect the anterior shell 131 to the posterior stmt 123 can allow some degree of pivoting of the strap member 129 relative to the posterior strut 123, which, in turn, allows the anterior shell 131 to float or move up and down with respect to the posterior strut position. This has the advantage of accommodating movement of the lower leg or pistoning of the calf during gait, making the orthosis 117 more comfortable.

According to an embodiment, the strap member 129 can include at least one reinforcement feature arranged to help maintain a vertical position of the strap member 129. This can be particularly advantageous for users who have suffered a stroke and consequently experience diminished upper body mobility or dexterity. These users may not have full use of both hands, making donning and/or doffing of an AFO more difficult. The reinforced strap member 129 facilitates alignment and/or securement of the strap member 129 with one hand during donning and/or doffing as the user is not required to lift the strap member 129 with one hand into a vertical position and secure the strap member 129 with the other hand. The reinforcement of the strap member 129 can also help maintain a vertical position of the anterior shell 131 attached to the strap member 129 during use.

According to an embodiment, the strap member can include a stiffening member 133. The stiffening member 133 can be integral or internal to the strap member 129. The stiffening member 133 can be inflexible. The stiffening member 133 can be inflexible vertically and flexible horizontally. The stiffening member 133 can be heat formable. The stiffening member 133 can be made of any suitable material including, but not limited to, a plastic material and/or a metal. For instance, the stiffening member 133 can be a thin plastic stiffener integrated into the strap member 129. The stiffening member 133 can comprise a semi-rigid plastic member interposed between two pieces of loop material. Using the stiffening member 133 with the anterior shell 131, can help prevent undesirable sag or migration of the strap member 129 down the user's leg, which would make the strap member 129 and the anterior shell 131 more difficult to secure. The stiffening member 133 can also strengthen the general construction by forming a more rigid connection between the strap member 129 and the base element 127.

According to a variation, the stiffening member 133 can include a set of holes along a length of the stiffening member 133 to allow a clinician or user to customize the length of the stiffening member 133 extending between the base element 127 and the anterior shell 131. This also allows the stiffening member 133 to provide an anchor point on the base element. According to a variation, the strap member 129 can define a liner or pocket for securing the strap member 129 to the base element 127.

In an embodiment, the strap member 129 can include a pair of end portions that are removably attached to the base element 127. This provides the ability to connect the strap member 129 on the left or right side of the user's leg, allowing the orthosis 117 to be customized for users or patients having function or dexterity in only a single hand. In other embodiments, the strap member 129 can include a single end portion that is removably attached to the base element 127. For instance, the strap member 129 can include a first end portion integral to the base element 127 and a second free end portion that can be removably attached to the base element 127 to secure the securing device 125 around the user's leg. In other embodiments, the strap member 129 can include one or more slots for removably attaching the strap member 129 to the base element 127 and/or the anterior shell 131.

According to a variation, the securing device 125 includes a height adjustment mechanism. For instance, the vertical position of the base element 127 and/or the anterior shell 131 can be adjustable relative to the posterior strut 123 to accommodate users with different tibial lengths. As seen in FIG. 15A, the base element 127 can define an internal sleeve 128 and a portion of the posterior strut 123 can be slidably received within the sleeve 128. The position of the base element 127 along a length of the posterior strut 123 can be adjustable. In an embodiment, the position of the base element 127 on the posterior strut 123 can be selectively fixed via a post member 124 connected to the base element 127 and arranged to selectively lock in a set of holes 126 defined in the posterior strut 123. The post member 124 can be spring loaded or biased to extend through the holes 126.

To adjust the vertical position of the base element 127 on the posterior strut 123, the post member 124 can be manually depressed to release the post member 124 from a hole 126, which, in turn, allows the base element 127 to slide along a length of the posterior strut 123 until the post member 124 locks into another selected one of the holes 126. According to a variation, the vertical position of the post member 124 within the sleeve 128 is fixed. In other embodiments, the vertical position of the post member 124 within the sleeve 128 is adjustable.

In other embodiments, the position of the base element 127 on the posterior stmt 123 can be selectively fixed via fasteners (e.g., rivets, screws, or bolts) insertable in a set of holes defined in the base element 127 and the posterior strut 123. The base element position and/or the anterior shell position can thus be customized based on patient anatomy, patient preference, AFO performance, etc. For example, the greater the distance between the securing device 125 and the footplate, the greater leverage the AFO is able to create.

In other embodiments, the securing device 125 can include one or more cushioning elements 150 (shown in FIG. 14) positioned on the inner surface of the anterior shell 131 and/or the inner surface of the base element 127 to increase comfort between the user's lower leg and the anterior shell 131, and absorb shock during use of the AFO.

According to a variation, the base element 127 can define an injection molded hook portion arranged to interact with a loop portion on the strap member 129. In other embodiments, the strap member 129 can be secured to the base element 127 via a cam buckle, a ratchet buckle, a dial tensioning mechanism with a tensioning element, or other suitable securement mechanisms. In yet other embodiments, the strap member 129 can be removably attached to the base element 127 and anterior shell 131 using an attachment mechanism comprising a rivet or Chicago screw.

The anterior shell 131 can be a light-weight, rigid or semi-rigid element and can be formed of carbon, a carbon or fiber composite, or any other suitable material. The anterior shell 131 can be made of a plastic material. In other embodiments, the anterior shell 131 can be made of a formable material, allowing the anterior shell 131 to be custom-molded to a specific patient's anatomy.

The rigidity and arrangement of the anterior shell 131 on the orthosis 117 helps the orthosis 117 respond better to forces during gait, which are typically forward (anterior), and reduces the potential for complications during gait where users lean back in the orthosis 117, negatively effecting balance and stability. Furthermore, the anterior shell 131 can help dissipate pressure from the strap member 129 that can result in discomfort and, in extreme cases, reduction in blood flow to the user's leg.

The anterior shell 131 can include different thicknesses to vary the flexibility of the anterior shell 131. For instance, the anterior shell 131 can include side portions with a relatively thinner thickness to allow for some medial and/or lateral flexing of the anterior shell 131. This can improve the fit of the anterior shell 131 on users with a wide range of calf circumferences.

Figure 16:
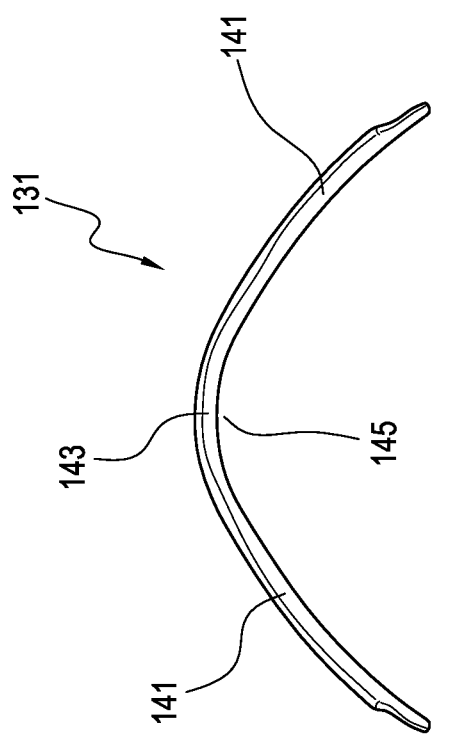
FIG. 16 is a top view of the anterior shell shown in FIG. 14.

Referring to FIG. 16, the anterior shell 131 can have any suitable shape but is shown having a v-shaped profile or configuration including side portions 141 that are angled relative to one another and converge together to form a peak 143. The side portions 141 can have a generally planar configuration while the anterior shell 131 at or near the peak 143 can define a contour. The inner surface of the anterior shell 131 along the peak 143 can be concavely curved.

As the anterior shell 131 is forced against the anterior of the lower leg during gait, the side portions 141 can engage the lower leg along the medial and lateral sides of the Tibial Crest and support the peak 143 over the Tibial Crest, which, in turn, allows the anterior shell 131 to exert or transfer a greater force on the lower leg along the medial and lateral sides of the Tibial Crest rather than directly on the Tibial Crest. This advantageously at least in part off-loads pressures on the Tibial Crest, thereby enhancing comfort of the orthosis 117.

The planar configuration of the side portions 141 increases the contact surface area between the anterior shell 131 and the lower leg. The peak 143 can define in part a relief zone 145 located along the inner surface of the anterior shell 131 over the Tibial Crest. The shape and material of the anterior shell 131 also provides flexibility to maximize fit on users with a wide range of calf circumferences.

The anterior shell 131 can define rolled top and bottom edges 135 and a cut-out 137 defined along the upper periphery of the anterior shell 131 for accommodating the Tibial Tuberosity. The rolled edges 135 and the cut-out 137 have the advantage of enhancing comfort, with the cut-out 137 also allowing for placement of the anterior shell 131 higher up on the lower leg by better accommodating the Tibial Tuberosity.

Optionally, the anterior shell 131 can define a second cut-out 139 along the lower periphery of the anterior shell 131. The anterior shell 131 can be vertically symmetrical. This can allow the anterior shell 131 to be inverted during fitting while still accommodating the Tibial Tuberosity, reducing user confusion. It also can make the orthosis 117 easier to configure during initial fitting, as the strap member 129 can be arranged to go medially or laterally by simply rotating the anterior shell 131. The anterior shell 131 can also have a shorter height defined between its upper and lower edges. In the illustrated embodiment, the height of the anterior shell 131 can be slightly greater than the height of the strap member 129 along the posterior strut 123. This beneficially limits pressure points with extreme calf shapes or where the calf shape flares dramatically from the anterior shell 131 to fit a greater range of calf shapes.

Figure 17:
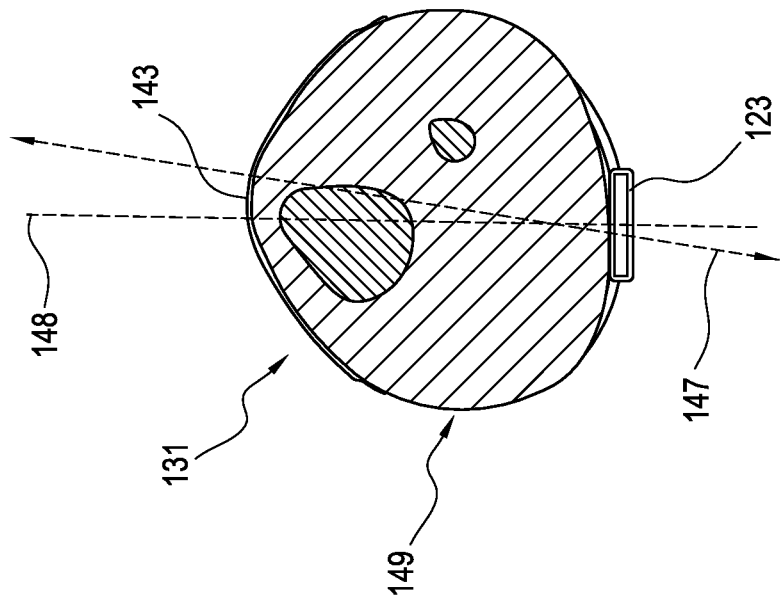
FIG. 17 is a cross section top view of the securing device shown in FIG. 14 during use.

As seen in FIG. 17, the peak 143 of the anterior shell 131 can be slightly medial of the longitudinal axis 147 of the foot or footplate and directly or substantially opposed the posterior strut 123 which can be slightly lateral of the longitudinal axis 147 of the foot. More particularly, as the Tibial Crest and Tibial Tuberosity are slightly medial of the longitudinal axis 147 of the foot during use, placement of the anterior shell 131 can directly oppose the posterior strut 123 placed slightly lateral of the longitudinal axis 147 of the foot. It will be appreciated that the line of progression 148 can be substantially aligned with the midline of the calf, and the anterior shell 131 and the posterior strut 123 are generally normal to the line of progression 148.

This beneficially limits medial and/or lateral migration of the posterior strut 123 and/or the anterior shell 131 during use, as neither is pulling the other either medially or laterally during gait. As indicated above, the anterior shell 131 can be generally aligned with the user's line of progression 148. It will be appreciated that the term aligned can mean that the anterior shell is substantially perpendicular to the line of progression or substantially centered on the line of progression. This has the advantage of helping to keep force during gait normal to the support structure of the orthosis 117, offering potential increases in gait efficiency and a reduced likelihood of premature failure, as well as potentially feeling more intuitive for new users.

The orthosis 117 including the anterior shell 131 directly opposite the posterior strut 123 can thus help the orthosis 117 respond better to forces during gait. Furthermore, a composite anterior shell 131 can dissipate pressure from fabric straps that can result in discomfort and, in extreme cases, reduction in blood flow to the leg.

Figure 19:
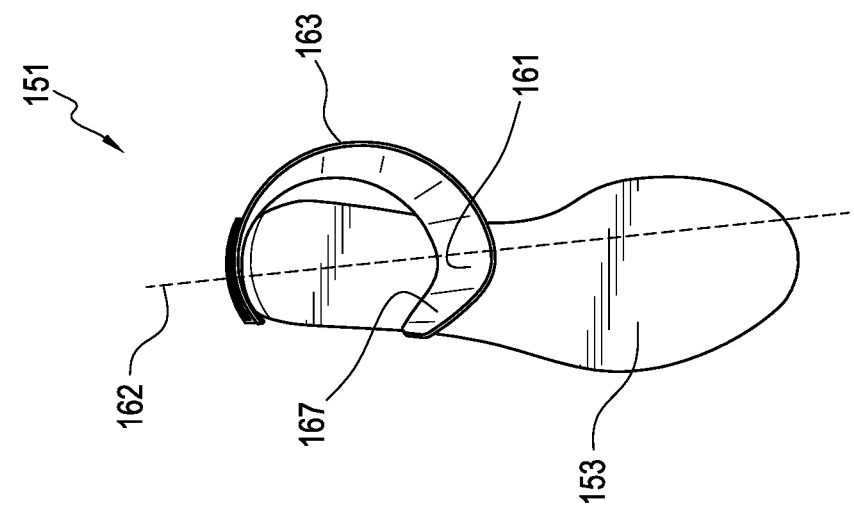
FIG. 19 is a top view of the orthotic system shown in FIG. 18.
Figure 18:
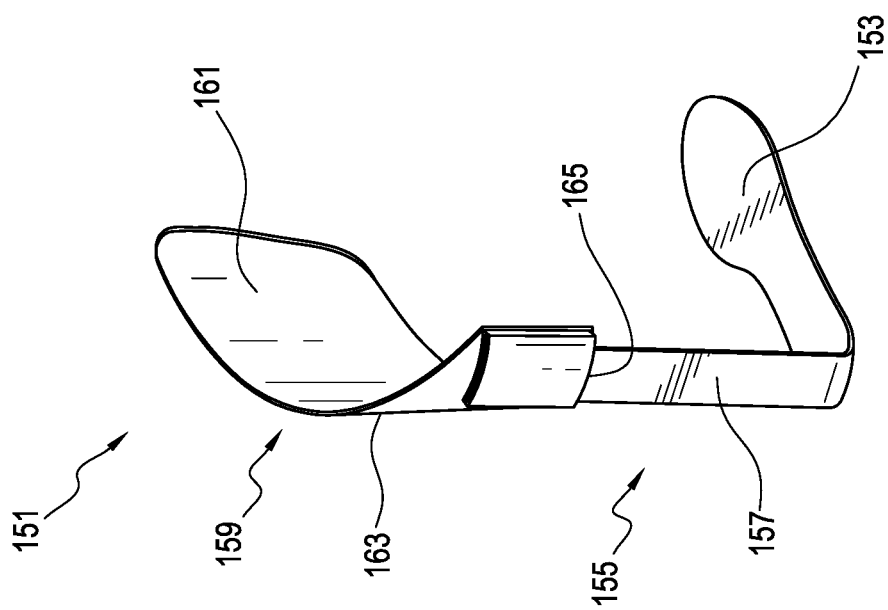
FIG. 18 is a perspective view of an orthotic system according to another embodiment.

FIGS. 18 and 19 show yet another embodiment of an orthotic system comprising an orthosis 151. The orthosis 151 comprises a footplate 153 and a leg support 155 including a posterior strut 157 constructed similarly to the previously described embodiments.

The orthosis 151 includes a securing device 159 for extending circumferentially around a user's leg and securing the orthosis 151 on the user's lower leg. The securing device 159 can include an anterior shell 161, a wrapping portion 163, and at least one strap member. The strap member is not shown for ease of reference.

As seen, the wrapping portion 163 and the anterior shell 161 can wrap around a portion of the user's lower leg, providing force transmission from the anterior shell directly to the posterior strut 157. The wrapping portion 163 can have a generally conical shape to correspond to the shape of the leg. The wrapping portion 163 can be integral to the anterior shell 161. The wrapping portion 163 can wrap from posterior to anterior. The wrapping portion 163 includes an open side, facilitating donning and doffing. The open side of the wrapping portion 163 can be on the medial or lateral side of the user's lower leg.

The anterior shell 161 can be directly opposed the posterior strut 157 placed slightly lateral of the longitudinal axis 147 of the foot (shown in FIG. 17). This has the advantage of limiting medial and/or lateral migration of the posterior strut 157 or anterior shell 161 during use, as neither is pulling the other either medially or laterally during gait. In addition, the anterior shell 161 is generally aligned with the line of progression 162 (shown in FIG. 19), helping to keep force during gait normal to the support structure of the orthosis 151.

On the posterior aspect, the wrapping portion 163 of the anterior shell 161 can be attached to the posterior strut 157 via a portion of the posterior strut 157 received in a sleeve 165 defined in the wrapping portion 163. In other embodiments, the wrapping portion 163 can be attached to the posterior strut 157 via a flexible connector, like an elastic band such that the wrapping portion 163 can move with the user's leg to accommodate pistoning of the calf with respect to the anterior shell during use and increase comfort. In other embodiments, the wrapping portion 163 can be connected to the posterior strut 157 via a rigid fastener, like a rivet or screw. The wrapping portion 163 of the anterior shell 161 can be connected at any location along a height of the posterior strut (e.g., high or low). The anterior shell 161 can be formed for the left or right leg and/or the medial or lateral aspect of the leg.

The anterior shell 161 can be contoured to a typical user leg shape or sized and shaped based on the patient's calf diameter and/or shape. For instance, the anterior shell 161 can define a flat contour portion 167 on the lateral side of the anterior shell 161. In other embodiments, the flat contour portion can be located on the medial side of the anterior shell 161 to accommodate or comfortably fit on the Tibial Crest.

Like the anterior shell 131, the anterior shell 161 can include a light-weight material, such as a carbon composite that limits force transmission loss during gait. The anterior shell 161 can be relatively thin to allow flexing to accommodate a range of calf diameters. To enhance flexibility, the composite material can include fiberglass, which is more flexible than carbon fiber composites.

FIG. 20 shows yet another embodiment of the orthotic system comprising a securing device 160 having an anterior shell 162 formed to be left/right and medial/lateral non-specific. A wrapping portion 164 and a base element 166 can be integral to the anterior shell 162. The anterior shell 162 can be reversible by flipping it over so that the wrapping portion 164 wraps around either the medial or lateral sides of either the left or right leg. The base element 166 can define a sleeve 168 arranged to receive and secure a portion of a posterior strut to the securing device 160. In an embodiment, the anterior shell 162 can include a height adjustment mechanism. For instance, the posterior strut 157 (shown in FIG. 18) and the base element 166 can be provided with multiple height adjustment holes 170, which are selectable during assembly to a height best suited for the patient.

According to a variation, the wrapping portion 164 can define a thin portion 172 between the anterior shell 162 and the base element 166 to facilitate flexing of the anterior shell 161, allowing it to adapt to a wider range of anatomies.

FIG. 21 shows yet another embodiment of an orthotic system comprising an orthosis 169. The orthosis 169 includes a footplate 171 and a leg support 173. The leg support 173 includes a lower lateral strut 175 connected to the lateral side of the footplate 171 and a lower medial strut 177 connected to the medial side of the footplate 171. The lower lateral and medial struts 175, 177 extend upwardly and curve or wrap inwardly around the user's ankle area to a location where they come together to form an upper posterior strut 179 above the heel area. The upper posterior strut 179 is arranged to extend along the posterior aspect of the user's lower leg or calf.

The orthosis 169 includes a securing device 181 for extending circumferentially around a user's leg and securing the orthosis 169 on the user's lower leg. The securing device 181 includes an anterior shell 183, a wrapping portion 185, and at least one strap member. The strap member is not shown for ease of reference. The wrapping portion 185 is arranged to spiral or wrap around a portion of the user's lower leg and can have a shape to generally correspond to the shape of the leg. The wrapping portion can be connected to or integral to the upper posterior strut 179.

The wrapping portion can be attached to the upper posterior strut via a flexible connection, such as via an elastic band. This may allow for some movement of the wrapping portion relative to the upper posterior strut, helping to accommodate pistoning of the calf with respect to the anterior shell during use. This also can make the AFO more comfortable. In other embodiments, the wrapping portion can be attached to the upper posterior strut via a rigid connection, like a rivet or screw.

The anterior shell 183 can be adjustably positioned on the wrapping portion 185. For instance, the anterior shell 183 can define a sleeve portion 187. The wrapping portion 185 can slidably extend through the sleeve portion 187 such that the anterior shell 183 can slide along a length of the wrapping portion 185. This allows the proximal, distal, lateral, and medial positions of the anterior shell 183 to be varied as the anterior shell 183 moves along the spiraling wrapping portion 185. In an embodiment, the anterior shell 183 can float along the wrapping portion 185 during use. In other embodiments, the position of the anterior shell 183 on the wrapping portion 185 can be varied and selectively fixed in a specific position.

The anterior shell 183 can be moved or rotated along the wrapping portion 185 to be in substantial alignment with the Tibial Crest of the patient, directly opposing the upper posterior strut 179. The anterior shell 183 can be moved along the wrapping portion 185 such that it is generally aligned with the user's line of progression (e.g. the line of progression 162 shown in FIG. 19), resulting in increased gait efficiency and reduced likelihood of premature failure.

In an embodiment, the upper posterior strut 179 can be slightly lateral of the longitudinal axis of the foot and the anterior shell 183 can be slightly medial of the longitudinal axis of the foot. This beneficially limits medial and/or lateral migration of the strut and anterior shell during use, as neither is pulling the other either medially or laterally during gait. This helps the orthosis 169 respond better to forces during gait and increasing user comfort.

The anterior shell 183 can be configured similarly to the previously described embodiments. For instance, the anterior shell 183 can include a light-weight material, such as a carbon composite that limits force transmission loss during gait. The anterior shell 183 can include one or more relatively thin sections to allow flexing in different areas. The anterior shell 183 can have any suitable shape and can define an inner surface contoured to a typical user leg shape or sized and shaped based on a patient's calf diameter and/or shape.

According to a variation, the anterior shell 183 can be vertically non-symmetrical. For instance, the anterior shell 183 can be taller on one side of the sleeve portion 187 than the other. This has the advantage of allowing the anterior shell 183 to be positioned on the wrapping portion 185 with the longer or larger surface on top for taller patients or with the smaller or shorter surface on top for shorter patients.

FIGS. 22-22B show yet another embodiment of an orthotic system comprising an orthosis 189. The orthosis 189 can be similar to the orthosis 169 including a footplate 191, a leg support 193, and a securing device 195 for extending circumferentially around a user's leg and securing the orthosis 189 on the user's lower leg.

The securing device 195 includes an anterior shell 197, a wrapping portion 199, and at least one strap member. The strap member is not shown for ease of reference. The wrapping portion 199 is arranged to spiral or wrap around a portion of the user's lower leg and can have a shape to generally correspond to the shape of the leg. The wrapping portion 199 can be connected to or integral to an upper posterior strut 201 of the leg support 193. The wrapping portion 185 can be attached to the upper posterior stmt 201 via a flexible connection or rigid connection.

Like the previous embodiment, the anterior shell 197 is adjustably positioned on the wrapping portion 199. For instance, the anterior shell 197 can be connected to the wrapping portion 199 via a sliding connection including a fastener 203 extending through the anterior shell 197 and a backing plate 205 located on the inner surface of the anterior shell 197.

The wrapping portion 199 can define a slot 207 slidably receiving the fastener 203 so that the position of the anterior shell 197 along the length of the slot is adjustable in a general lateral/medial direction.

The anterior shell 197 can define a slot 209 slidably receiving the fastener 203 so that the position of the anterior shell 197 along the length of the slot is also adjustable in a general proximal/distal. This provides a height adjustment mechanism that allows the anterior shell 197 to be placed in a more comfortable position on the patient's lower leg. Moreover, the overall arrangement of the orthosis 189 allows the anterior shell 197 to be customized in the medial/lateral and proximal/distal directions.

According to a variation, the anterior shell 197 is arranged to rotate or swivel about the fastener member 203 so that the anterior shell 197 can better move with the lower leg. The anterior shell 197 can be moved to be in substantial alignment with the Tibial Crest or directly opposing the upper posterior strut 201.

The anterior shell 197 can be constructed similarly to the previously described embodiments. For instance, the anterior shell 197 can include a light-weight, rigid or semi-rigid material, such as a carbon composite. The anterior shell 197 can have any suitable shape but is shown having a shield like shape. The inner surface of the anterior shell 197 can be contoured to a typical leg shape or sized and shaped base on a patient's calf diameter and/or shape. Optionally, the anterior shell 197 can be integrated into a soft goods member 211, increasing user comfort.

Figure 24:
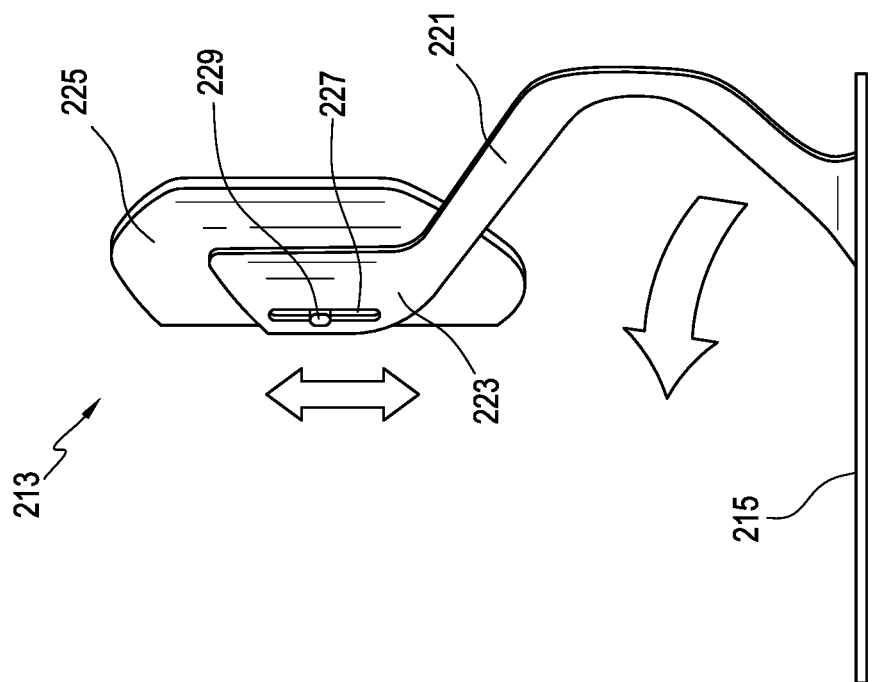
FIG. 24 is a side view of the system shown in FIG. 23.
Figure 23:
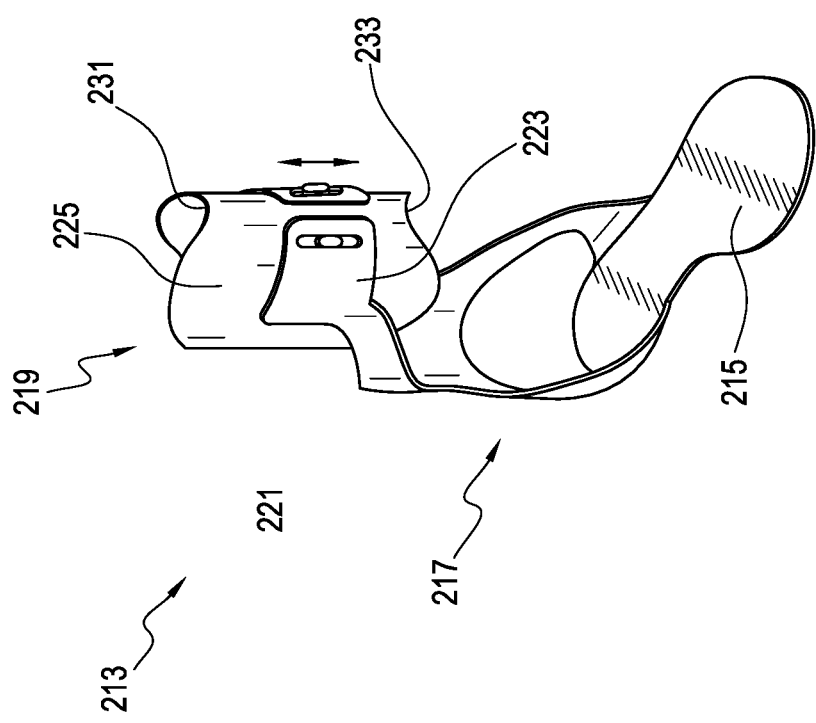
FIG. 23 is a perspective view of an orthotic system according to another embodiment.

FIGS. 23 and 24 show yet another embodiment of an orthotic system comprising an orthosis 213. The orthosis 213 can be similar to the previously described embodiments including a footplate 215, a leg support 217, and a securing device 219 for extending circumferentially around a user's leg and securing the orthosis 213 on the user's lower leg.

The securing device 219 can include a pair of lateral and medial anterior struts 221 extending from the leg support 217. Each of the lateral and medial anterior struts 221 wraps around a side of the user's lower leg and includes an attachment portion 223 arranged to be situated over the anterior aspect of the lower leg. The lateral and medial anterior struts 221 can be integral to or connected to the leg support 217. In an embodiment, the leg support 217 is arranged to flex so that the securing device 219 can move in the anterior/posterior direction.

An anterior shell 225 is adjustably attached to the attachment portions 223 of the lateral and medial anterior struts 221. The anterior shell 225 can be arranged on the lateral and medial anterior struts 221 so that it is generally aligned with the user's line of progression (e.g., the line of progression 162 shown in FIG. 19), resulting in greater gait efficiency and a more natural feel.

In an embodiment, the anterior shell 225 is attached to the attachment portions 223 via a sliding mechanism. For instance, each of the attachment portions 223 can define a generally vertical slot 227. The anterior shell 225 can include a pair of connectors 229 (e.g., screws, rivets, pins) slidably received in the vertical slots 227. This can allow the anterior shell 225 to float or move in the proximal/distal direction and/or can provide a height adjustment mechanism.

In other embodiments, the anterior shell 225 can be connected to the attachment portions 223 via a flexible connection (e.g., an elastic band) to allow proximal/distal motion of the anterior shell 225 to accommodate pistoning of the calf during walking. In other embodiments, the anterior shell 225 can include a pair of connectors 229 slidably received in the vertical slots 227 and including elastic bumpers disposed between the attachment portion 223 and the anterior shell 225 to help accommodate pistoning of the calf during walking.

The anterior shell 225 can be configured similarly to the previously described embodiments. The anterior shell 225 can be formed of a carbon composite material that limits force transmission loss during gait. The anterior shell 225 can be formed of a resin material such as a plastic material. The anterior shell 225 can be shaped to generally correspond to the anterior aspect of the user's lower leg including a pair of side portions wrapping around the sides of the user's leg. The anterior shell 225 can define a cut-out 231 along its upper periphery and/or a cut-out 233 along its lower periphery to help relieve pressure along the Tibial Crest during use.

According to a variation, the anterior shell 225 can include padding or cushioning material along its inner surface to increase user comfort. The securing device 219 can include at least one strap member (not shown). In an embodiment, the securing device 219 can include a single strap member attached to the anterior shell 225. In other embodiments, the securing device 219 can include a dual strap configuration for accommodating different calf sizes. In yet other embodiments, the anterior shell 225 can be integral to the leg support 217.

Figure 26:
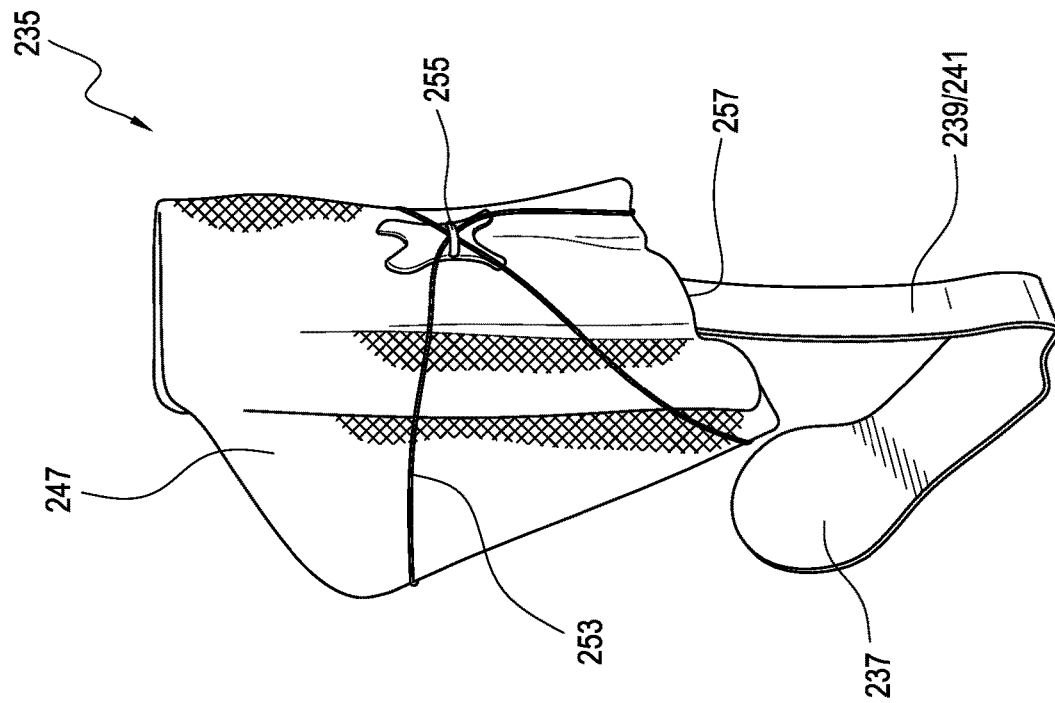
FIG. 26 is a back view of the system shown in FIG. 25.
Figure 25:
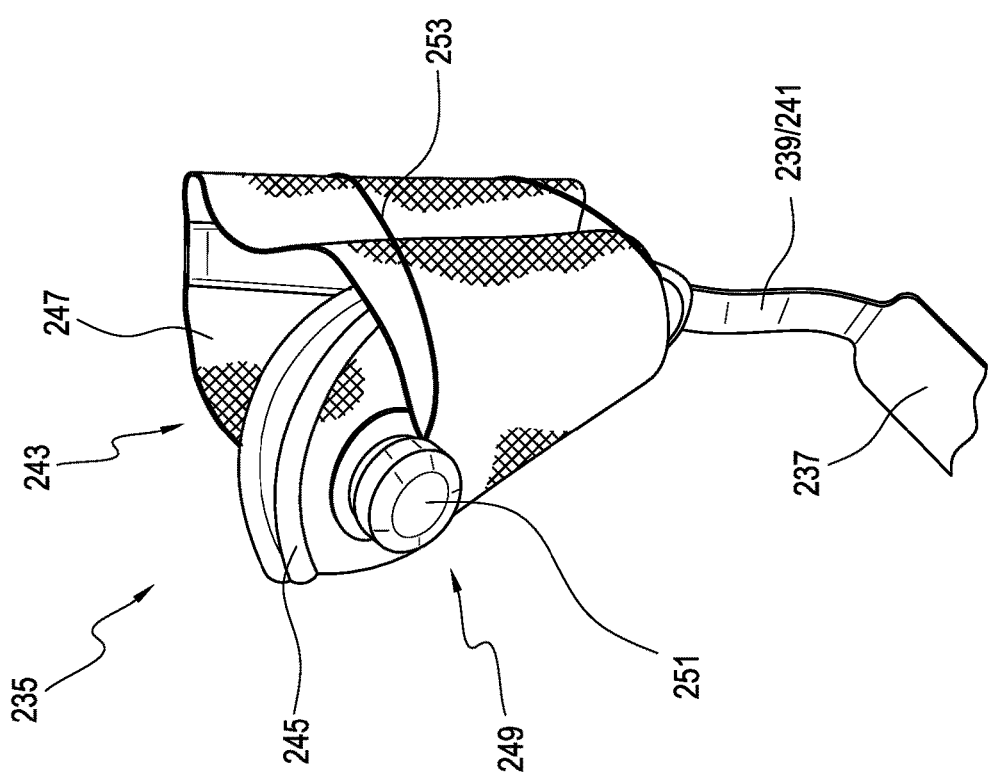
FIG. 25 is a perspective view of an orthotic system according to another embodiment.

FIGS. 25 and 26 show yet another embodiment of an orthotic system comprising an orthosis 235. The orthosis 235 includes a footplate 237 and a leg support 239 including a posterior strut 241 constructed similarly to the previously described embodiments. For instance, the posterior strut 241 can include a connecting portion normal to the line of progression and slightly lateral of the longitudinal axis of the user's foot.

The orthosis 235 includes a securing device 243 for extending around a user's leg and securing the orthosis 235 on the user's lower leg. The securing device 243 can include an anterior shell 245, a sleeve 247, and a tightening system 249.

The sleeve 247 includes a posterior aspect attached to the posterior strut 241 and arranged to radially compress against the outer surface of the user's lower leg. The sleeve 247 is preferably formed from a material different from the anterior shell 245. A proximal portion of the posterior strut 241 can be disposed within a pocket or pouch 257 defined by the sleeve 247. The sleeve 247 can include a hook and loop closure system, providing adjustability.

The sleeve 247 is preferably formed from a textile and the anterior shell 245 is formed from a rigid or semi-rigid material. The sleeve 247 is preferably more flexible and elastic than the anterior shell 245 such that the sleeve 247 retracts to an original size upon release of tension of the sleeve.

The sleeve 247 is preferably configured and dimensioned to be securely tensioned over the lower leg. The sleeve 247 may have a diameter less than a diameter of the lower leg such that the sleeve 247 stretches over and is tensioned when selectively placed over the outer surface of the lower leg.

The anterior shell 245 can be attached to sleeve 247 at any suitable location but is shown attached to the inner surface of the sleeve 247 along its anterior aspect. As such, the anterior shell 245 is attached to the posterior strut 241 via the sleeve 247.

Using the sleeve 247 to connect the anterior shell 245 to the posterior strut 241 can allow some degree of pivoting or movement of the sleeve 247 relative to the posterior strut 241, which, in turn, allows the anterior shell 245 to float with respective to the posterior strut position. This has the advantage of accommodating pistoning of the calf during gait, making the orthosis more comfortable.

A center of the anterior shell 245 can be slightly medial of the longitudinal axis of the user's foot and directly or substantially opposed the posterior strut 241 which is slightly lateral of the longitudinal axis of the user's foot. This advantageously helps limit medial and/or lateral migration of the posterior strut and/or the anterior shell during use. In addition, the anterior shell 245 is generally aligned with the user's line of progression (e.g., the line of progression 162 shown in FIG. 19). This helps to keep force during gait normal to the support structure of the orthosis and offers potential increases in gait efficiency.

The anterior shell 245 can have any suitable shape but is shown having a rounded wedge shape that tapers in the distal direction. The anterior shell 245 can be a light-weight, rigid or semi-rigid element and can be formed of carbon, a carbon composite, or any other suitable material. The anterior shell 245 can be made of formable material that can be customized to the shape of the anterior aspect of the user's lower leg. The anterior shell 245 can be made from a formable cast material disposed within a pouch. The anterior shell 245 can be made from a heat formable plastic, a closed cell polyethylene foam, or any other suitable formable material. The anterior shell 245 can include soft goods along its inner surface to increase user comfort.

According to a variation, a tightening system 249 can be incorporated with the sleeve 247 to help secure the anterior shell 245 to the posterior strut 241. For instance, the tightening system 249 can include a dial tensioner 251 secured to the anterior shell 245 and a cable 253 extending between the dial tensioner 251 and the posterior aspect of the sleeve 247. The cable 253 can be a cable, lace, wire or any other suitable member and may refer to a relatively long and relatively thin shaped metals or polymers, which may be single strand or multi-strand, and which may include friction coatings thereon. In other embodiments, the dial tensioner 251 can be secured to the posterior strut 241. In other embodiments, the tightening system 249 can include a plurality of dial tensioners. For example, the tightening system 249 can include a first dial tensioner near a top of the sleeve 247 and a second dial tensioner near a bottom of the sleeve 247.

In an embodiment, the cable 253 can wrap around the outside of the sleeve 247 through a cable guide 255 on the posterior aspect of the sleeve 247 and one or more cable guides on the distal portion of the anterior shell 245. According to a variation, the cable 253 can be integrated with one or more strap members as it extends between the anterior and posterior of the sleeve 247, reducing the likelihood of lines of pressure across the calf. As seen, the cable 253 can crisscross on the posterior aspect of the sleeve 247 although other arrangements are possible. The dial tensioner 251 may be rotated in a first direction to decrease the length of the cable 253 and thereby tighten the sleeve 247 on the lower leg. To increase the length of the cable 253 and thereby loosen the sleeve 247 on the lower leg, the dial tensioner 251 can be rotated in a second direction. The tightening system 249 also allows the cable 253 to be fixed at a defined or desired length.

FIGS. 27-30 show yet another embodiment of an orthotic system comprising an orthosis 265. The orthosis 265 can be similar to the previously described embodiments including a footplate 267 arranged to be positioned under a user's foot 266, a leg support comprising a posterior strut 269 arranged to extend along the posterior aspect of the user's lower leg 268, and a securing device 271 for extending around the lower leg 268 and securing the orthosis 265 on the user's lower leg 268. The securing device 271 can include an anterior assembly 273 and a base unit 275 connected to the posterior strut 269.

The anterior assembly 273 can be arranged along the anterior aspect of the lower leg 268 and includes an upper anterior shell 273a, a middle anterior shell 273b, and a lower anterior shell 273c. Each of the anterior shells 273a, 273b, and 273c are separate and comprise a rigid or semi-rigid member wrapping around the sides of the lower leg 268. The inner surface of the anterior shells 273a, 273b, 273c can be contoured to a typical leg shape or sized and shaped based on a patient's calf diameter and/or shape. A soft good member 299 can be provided on the inner surface of the anterior shells 273a, 273b, 273c, providing comfort and a proper fit of the securing device 271. The soft good member 299 can be made from any suitable material. The anterior shells may be formed of a carbon fiber composite, a plastic material, combinations thereof, or any other suitable material.

The anterior shells 273a, 273b, and 273c are spaced apart and connected by at least one strut member 297. The strut member 297 can be attached to the anterior shells 273a, 273b, and 273c via sleeve portions defined in the shell members of the anterior shells 273a, 273b, and 273c. Because the anterior shells 273a, 273b, and 273c are separate and spaced apart, the anterior shells 273a, 273b, and 273c can move independently of one another during gait, providing a more comfortable fit. This also can allow for some degree of pivoting or movement of the anterior shells 273a, 273b, and 273c relative to the posterior strut 269, which, in turn, allows the anterior assembly 273 to float with respect to the posterior strut position, making the orthosis 265 more comfortable.

The securing device 271 can include the base unit 275 connected to the posterior strut 269 and arranged along the posterior aspect of the lower leg 268. The base unit 275 is preferably formed from a material different than the anterior assembly 273. A proximal end portion of the posterior strut 269 can be disposed within a pouch or sleeve defined by the base unit 275. The base unit 275 is preferably formed from a textile that is more flexible than the anterior assembly 273.

Figure 30:
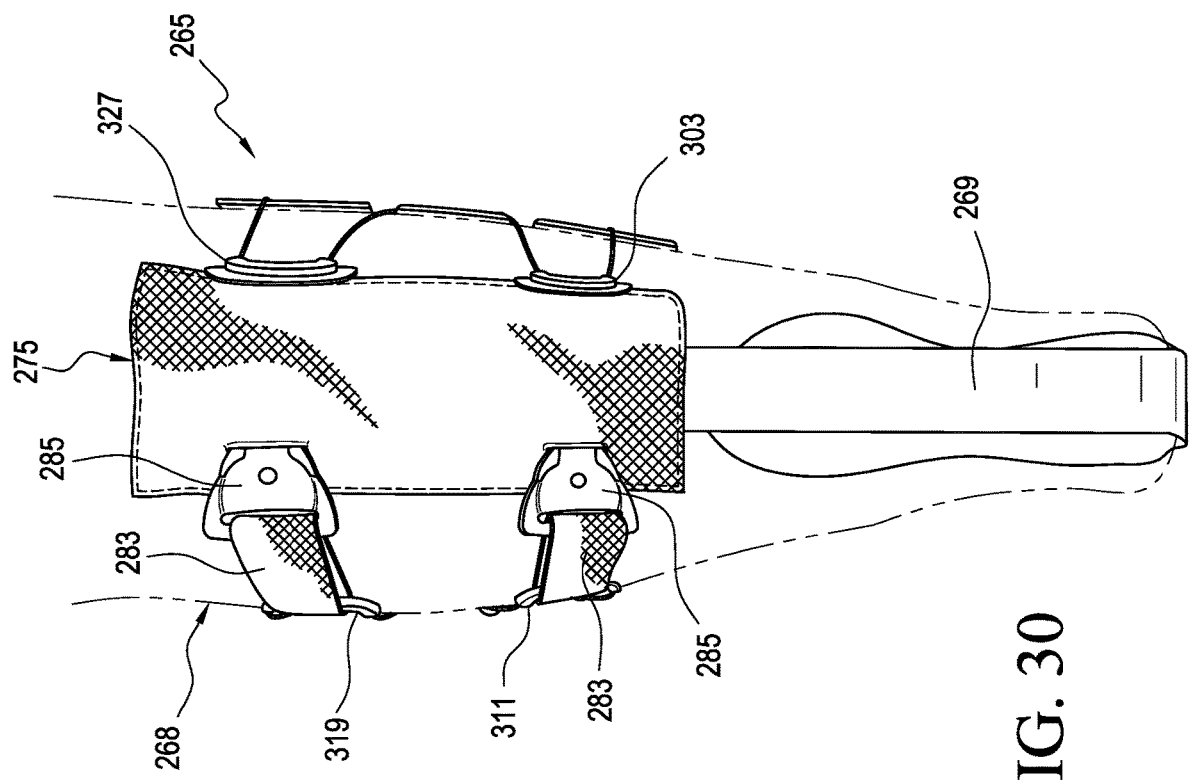
FIG. 30 is a back view of the system shown in FIG. 27.

Referring to FIG. 30, the anterior assembly 273 is operatively attached to the base unit 275 via a pair of strap members 283. Each of the strap members 283 can be removably and repeatedly attached to the base unit 275 via a connector 285. The connectors 285 can comprise locking clips, magnetic clips or any other suitable type of connector. When the connectors 285 are detached from the base unit 275, the securing device 271 opens up to form an open side on the orthosis 265, facilitating donning or doffing. This open side can be on the medial or lateral side of the lower leg 268.

Figure 29:
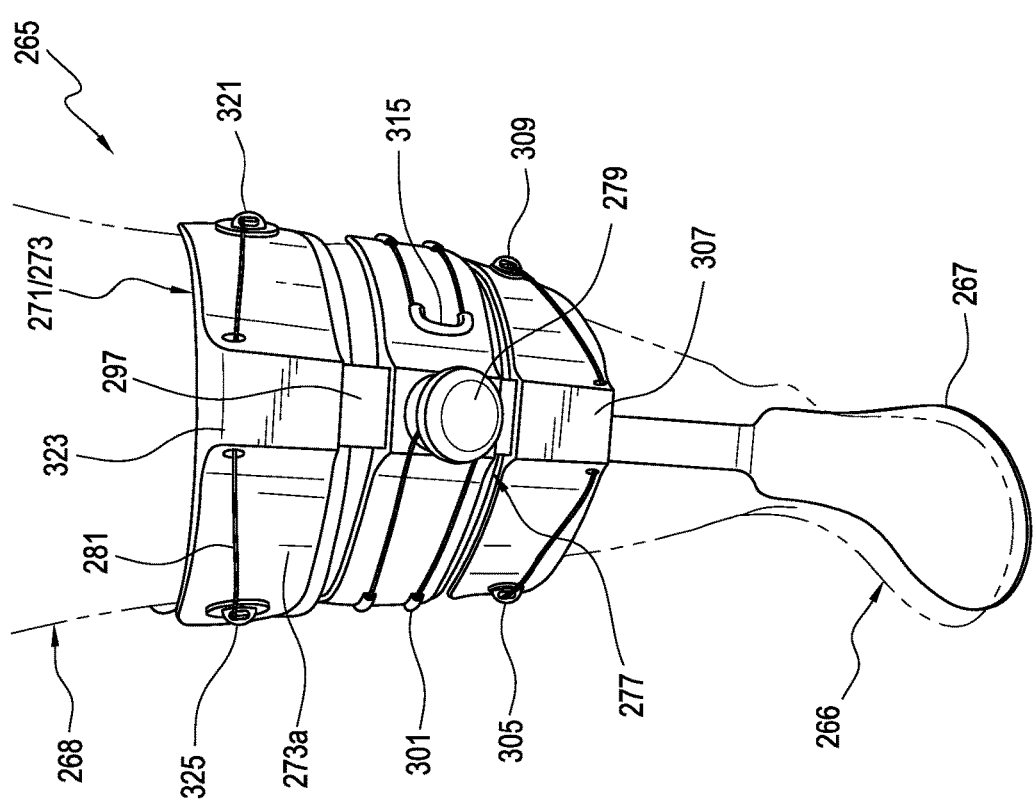
FIG. 29 is a front view of the system in FIG. 27.

According to a variation, a tightening system 277 can be incorporated with the anterior assembly 273 to help secure the securing system 271 to the user's lower leg 268. Referring to FIGS. 29 and 30, the tightening system 277 can include a dial tensioner 279 secured to the middle anterior shell 273b and a cable 281 extending between the dial tensioner 279 and the base unit 275. The cable 281 can be configured similarly to the cable of the previous embodiments. In other embodiments, the dial tensioner 279 can be secured to the posterior strut 269. In other embodiments, the tightening system 277 can include a plurality of dial tensioners. For instance, the tightening system 277 can include a first dial tensioner attached to the upper anterior shell 273a and a second dial tensioner attached to the lower anterior shell 273c.

In an embodiment, the cable 281 can wrap around the outside of the securing device 271 through a plurality of cable guides on the anterior assembly 273, the base unit 275, and the strap members 283. The dial tensioner 279 may be rotated in a first direction to decrease the length of the cable 281 and thereby tighten the securing system 271 on the lower leg 268. To increase the length of the cable 281 and thereby loosen the securing system 271 on the lower leg 268, the dial tensioner 279 can be rotated in a second direction. The tightening system 277 also allows the cable 281 to be fixed at a desired length.

Figure 28:
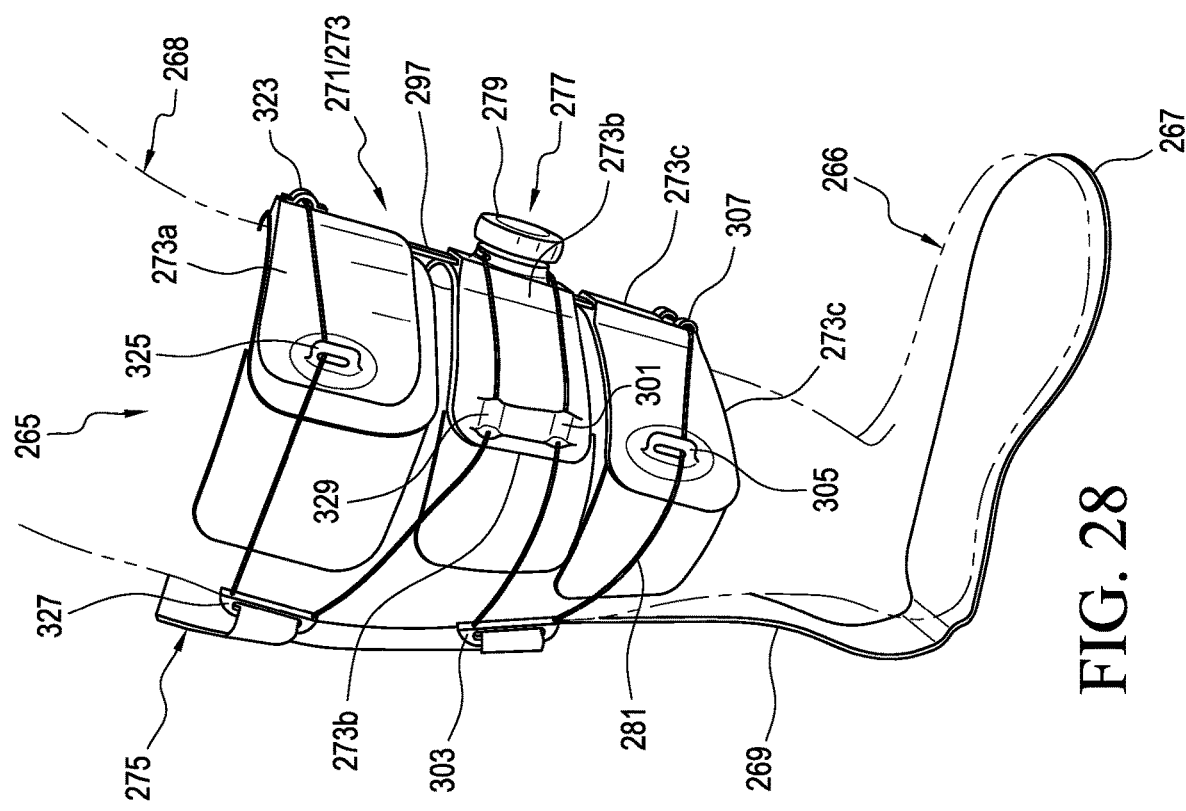
FIG. 28 is another perspective view of the system in FIG. 27.

As seen in FIGS. 28 and 29, the cable 281 extends from the dial tensioner 279 through a first guide 301 located on a side portion of the middle anterior shell 273b and a second guide 303, which, in turn, directs the cable 281 toward a third guide 305 located on a side portion the lower anterior shell 273c. The first guide 301 can comprise a channel formed on or in the shell member of the middle anterior shell 273b. The first guide 301 can extend along a generally linear line. The second guide 303 can be defined through a ring member connected to the base element 275. The third guide 305 can be defined by an eyelet attached to the lower anterior shell 273c.

Figure 27:
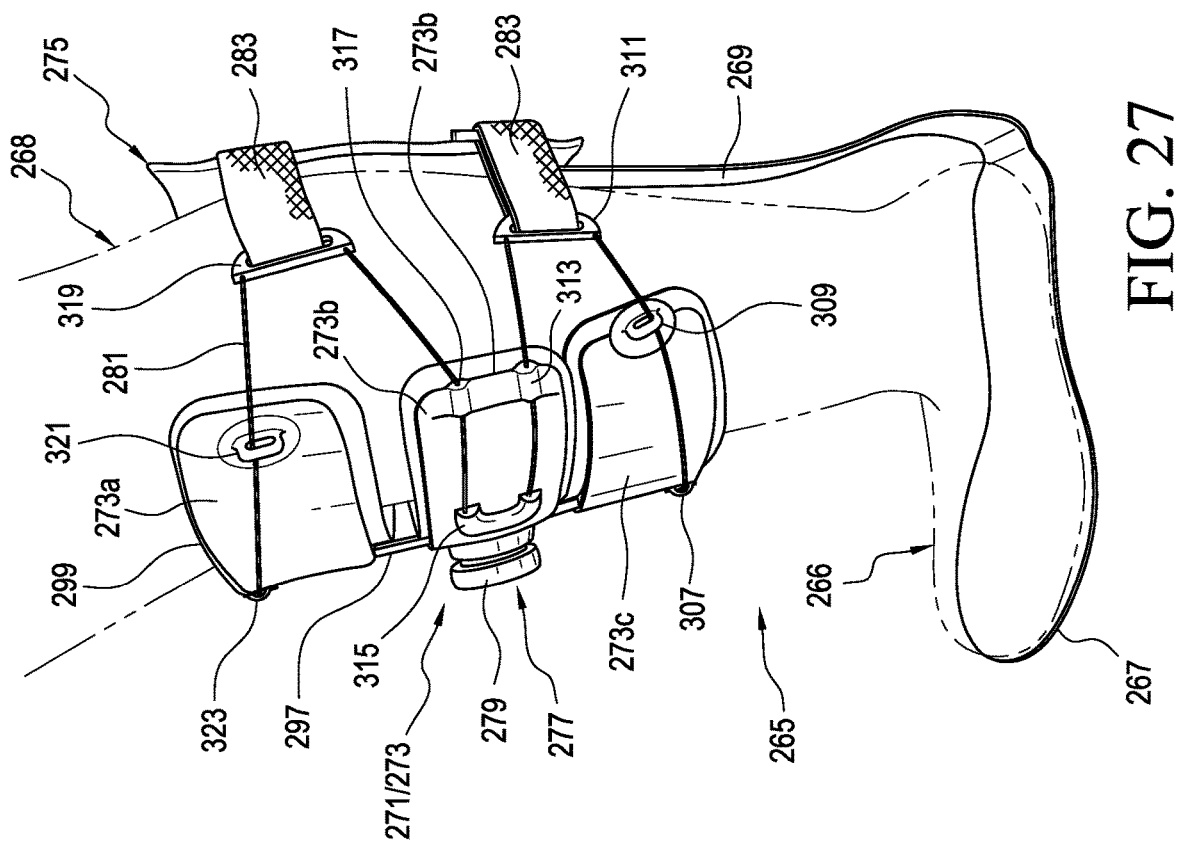
FIG. 27 is a perspective side view of an orthotic system according to another embodiment.

From the third guide 305, the cable 281 passes through a fourth guide 307 located at or near a center of the lower anterior shell 273c. As seen in FIGS. 27 and 29, the fourth guide 307 directs the cable 281 toward a fifth guide 309 located on the lower anterior shell 273c generally opposite the third guide 305. The fourth guide 307 can comprise an internal channel formed in the lower anterior shell 273c. The fifth guide 309 can be configured similar to the third guide 305.

As seen in FIGS. 27 and 30, the cable 281 extends from the fifth guide 309 toward a sixth guide 311, which, in turn, directs the cable 281 through a seventh guide 313 located on a side of the middle anterior shell 273b opposite the first guide 301. The sixth guide 311 can be defined through a ring member attached to the lower strap member 283. The seventh guide 313 can be configured similar to the first guide 301.

The seventh guide 311 directs the cable 281 through an eighth guide 315 located on the middle anterior shell 273b which directs the cable 281 through a ninth guide 317 located on the middle anterior shell 273b generally above the seventh guide 313. The eighth guide 315 can be a curved or turn-around channel formed on or in the middle anterior shell 273b near the dial tensioner 279. The ninth guide 317 can be configured similar to the seventh guide 311.

From the ninth guide 317, the cable 281 is directed to a tenth guide 319 defined by a ring attached to the upper strap member 283, which, in turn, directs the cable 281 through an eleventh guide 321 located on a side portion of the upper anterior shell 273a. The tenth guide 319 can be configured similar to the sixth guide 311. The eleventh guide 321 can be configured similar to the fifth guide 309.

From the eleventh guide 321 the cable 281 passes through a twelfth guide 323 (best shown in FIG. 29) located at or near a center of the upper anterior shell 273a. As seen in FIG. 28, the twelfth guide 323 then directs the cable 281 toward a thirteenth guide 325 located on an opposite side of the upper anterior shell 273a from the eleventh guide 321. The twelfth guide 323 can be configured similar to the fourth guide 307. Further, the thirteen guide 325 can comprise an eyelet like the eleventh guide 321.

The cable 281 extends from the thirteenth guide 325 toward a fourteenth guide 327, which, in turn, directs the cable 281 through a fifteenth guide 329 located on the middle anterior shell 273c generally above the first guide 301. The fourteenth guide 325 can be configured similar to the second guide 303 and the fifteenth guide 329 can be configured similar to the first guide 301.

The fifteenth guide 329 directs the cable 281 back toward the dial tensioner 279 where it is attached to the dial tensioner 279.

The dial tensioner 279 can be rotated in a first direction such that a portion of the cable 281 is wound about the dial tensioner 279, shortening the length of the cable 281 extending between the anterior assembly 273 and the base unit 275. This in turn can pull the anterior assembly 273 toward the posterior strut 269, which, in turn, causes the anterior assembly 273 to apply a load on the anterior aspect (e.g., tibia) of the lower leg 268 as the circumference the securing device 271 forms decreases. It will be appreciated that such applied loads can be used in securing the orthosis 265 on the lower leg 268 and/or controlling movement of the lower leg 268 and/or foot 266.

The dial tensioner 279 can also be rotated in a second direction opposite the first such that a portion of the cable 281 is unwound from the dial tensioner 279, lengthening the length of the cable 281 extending between the anterior assembly 273 and the base unit 275.

It will be appreciated that the embodiments described herein are to be regarded as exemplary only, as any orthotic system is possible. For instance, the heel portion of the footplate can include a thinner layer of carbon fiber and/or may be biased toward the foot bed of the shoe, allowing the heel portion to flex more during heel strike. Furthermore, it will be appreciated that the anterior shell of the orthosis embodiments can be utilized with other orthotic systems and/or orthopedic systems. For instance, the anterior shell can be incorporated in a knee brace and/or a walker boot.

In addition, while the line of progression is shown being linear, in other embodiments, the line of progression can turn or curve in one or more directions. While the footplate is shown having a peripheral shape generally corresponding to an entire foot, in other embodiments, the footplate can have a peripheral shape that generally corresponds to a portion of the foot. For instance, the forefoot portion can define a cutout so that when the foot is placed on the footplate, the forefoot portion does not extend completely below the phalanges or toes of the user.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. An orthosis for supporting a lower leg including a knee, an ankle, and a foot, the orthosis comprising:
    a footplate having a heel portion including a heel end, a midfoot portion, a longitudinal axis extending between the heel end and the midfoot portion;
    a line of progression extending from the heel end through the midfoot portion; and
    a posterior strut having a connecting portion connected to the heel portion of the footplate and extending upwardly therefrom, the connecting portion eccentrically connected to the heel end such that when the foot of a user is positioned on the footplate the connecting portion and the posterior strut are parallel to a rotation axis of the knee and obliquely oriented relative to a rotation axis of the ankle to accommodate a defined rotation of the foot and the longitudinal axis of the footplate relative to the line of progression during gait.

2. The orthosis of claim 1, wherein the defined rotation of the foot relative to the line of progression comprises the foot being externally rotated relative to the line of progression.

3. The orthosis of claim 1, wherein the connecting portion is integral to the posterior strut.

4. The orthosis of claim 1, wherein a thickness of the footplate through a first deflection zone defined along a length of the footplate is tapered to direct flexing of the footplate toward under heads of metatarsal bones of the foot.

5. The orthosis of claim 4, wherein a thickness of the first deflection zone along a forefoot portion of the footplate is less than about 0.4 times a thickness of the footplate along the heel portion.

6. The orthosis of claim 4, wherein a thickness of the first deflection zone varies by more than about 40% from a toe end of the footplate to between about 0.2 and about 0.4 of an overall length of the footplate.

7. The orthosis of claim 4, wherein the footplate comprises a supportive zone posterior of the first deflection zone, the supportive zone having a rigidity arranged to limit or resist involuntary plantarflexion of the foot of the user.

8. The orthosis of claim 7, wherein the supportive zone is arranged to extend under a center of mass of the foot of the user.

9. The orthosis of claim 4, further comprising a second deflection zone defined along a length of the posterior strut proximal of the connecting portion, the connecting portion being rigid and the posterior strut being arranged to flex through the second deflection zone during gait to accommodate voluntary plantarflexion of the foot of the user.

10. The orthosis of claim 9, wherein the second deflection zone extends along between about 40% and about 60% of an overall length of the posterior strut.

11. The orthosis of claim 1, wherein the footplate comprises a forefoot portion curving or angling upwardly from the midfoot portion of the footplate toward a toe end.

12. The orthosis of claim 1, wherein the connecting portion is integral to the posterior strut and defines a curved profile in a heel area of the user.

13. The orthosis of claim 1, wherein the connecting portion is a separate member from the posterior strut and the heel portion of the footplate.

14. An orthosis for supporting a lower leg including a knee, an ankle, and a foot, the orthosis comprising:
    a footplate having a heel portion including a heel end, a midfoot portion, a longitudinal axis extending between the heel end and the midfoot portion, and a deflection zone defined along a length of the footplate and through which the footplate is arranged to flex to accommodate dorsiflexion of the foot of a user positioned on the footplate;
    a line of progression extending from the heel end through the midfoot portion; and
    a posterior strut having a connecting portion connected to the heel portion of the footplate and extending upwardly therefrom, the connecting portion eccentrically connected to the heel end such that when the foot of the user is positioned on the footplate the connecting portion and the posterior strut are parallel to a rotation axis of the knee and obliquely oriented relative to a rotation axis of the ankle to accommodate a defined rotation of the foot and the longitudinal axis of the footplate relative to the line of progression during gait.

15. The orthosis of claim 14, wherein the footplate comprises a supportive zone posterior of the deflection zone, the supportive zone having a rigidity arranged to limit or resist involuntary plantarflexion of the foot of the user.

16. The orthosis of claim 15, wherein the supportive zone is arranged to extend under a center of mass of the foot of the user.

17. The orthosis of claim 14, wherein a thickness of the footplate through the deflection zone is tapered along the length of the footplate.

18. The orthosis of claim 14, wherein the connecting portion is integral to the posterior strut and defines a curved profile in a heel area of the user.

* * * * *